US009670530B2

(12) United States Patent
Kostem et al.

(10) Patent No.: US 9,670,530 B2
(45) Date of Patent: Jun. 6, 2017

(54) HAPLOTYPE RESOLVED GENOME SEQUENCING

(71) Applicant: Illumina, Inc., San Diego, CA (US)

(72) Inventors: Emrah Kostem, San Diego, CA (US); Sasan Amini, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 661 days.

(21) Appl. No.: 14/169,056

(22) Filed: Jan. 30, 2014

(65) Prior Publication Data

US 2015/0211054 A1    Jul. 30, 2015

(51) Int. Cl.
| | |
|---|---|
| *G01N 33/50* | (2006.01) |
| *C12Q 1/68* | (2006.01) |
| *G06F 19/18* | (2011.01) |
| *G06F 19/22* | (2011.01) |

(52) U.S. Cl.
CPC ......... *C12Q 1/6809* (2013.01); *C12Q 1/6869* (2013.01); *C12Q 1/6874* (2013.01); *G06F 19/18* (2013.01); *G06F 19/22* (2013.01)

(58) Field of Classification Search
None
See application file for complete search history.

(56) References Cited

U.S. PATENT DOCUMENTS

2016/0306922 A1*  10/2016  van Rooyen ........... G06F 19/28

FOREIGN PATENT DOCUMENTS

| | | |
|---|---|---|
| WO | WO2013/062856 A1 | 5/2013 |
| WO | WO2014/142850 A1 | 9/2014 |

OTHER PUBLICATIONS

Kinde, I. et al. "Detection and quantification of rare mutations with massively parallel sequencing," *Proceedings of the National Academy of Sciences*, vol. 108, No. 23, Jun. 7, 2011, pp. 9530-9535.

Duitama, J., et al. "ReFHap: a reliable and fast algorithm for single individual haplotyping," *Proceedings of the First ACM International Conference on Bioinformatics and Computational Biology*, Niagara Falls, NY, USA, 2010, pp. 160-169.
Bansal, V. et al. "HapCUT: an efficient and accurate algorithm for the haplotype assembly problem," *Bioinformatics*, ECCB 2008 Conference Proceedings, Sep. 22-26, 2008, Cagliari, Italy, vol. 24, No. 16, pp. i153-i159.
Abecasis, G.R., et al. (The 1000 Genomes Project Consortium) "A map of human genome variation from population-scale sequencing," *Nature*, vol. 467, No. 7319, Oct. 28, 2010, pp. 1061-1073.
Eskin, E. et al. "A note on phasing long genomic regions using local haplotype predictions," *Journal of Bioinformatics and Computational Biology*, vol. 4, No. 3, Jun. 2006, pp. 639-647.
He, D. et al. "Optimal algorithms for haplotype assembly from whole-genome sequence data," *Bioinformatics*, vol. 26, No. 12, Jun. 2010, pp. 183-190.
Caruccio, N. "Preparation of next-generation sequencing libraries using Nextera™ technology: simultaneous DNA fragmentation and adaptor tagging by in vitro transposition," in High-Throughput Next Generation Sequencing: Methods and Applications (Kwon and Ricke eds.), *Methods in Molecular Biology*. vol. 733. May 25, 2011. pp. 241-255.
Adey, A., et al. "Rapid, low-input, low-bias construction of shotgun fragment libraries by high-density in vitro transposition," *Genome Biology*, vol. 11, No. 12, Dec. 8, 2010, pp. 17.

* cited by examiner

*Primary Examiner* — Jason Sims
(74) *Attorney, Agent, or Firm* — Weaver Austin Villeneuve & Sampson LLP

(57) ABSTRACT

Methods of determining a haplotype or partial haplotype of a DNA sample containing high molecular weight segments of genomic DNA are disclosed. Such methods may include sequencing DNA in an enriched DNA sample to produce a plurality of sequence reads, where some of the sequence reads contain a first allele of the first haplotype and other of the sequence reads contain a second allele of the first haplotype. Some methods align the sequence reads to a reference genome to produce aligned reads, where aligned reads from the first high molecular weight segment tend to cluster into islands on the reference genome. Some methods further determine distances separating adjacent aligned reads on the reference genome and select a first group of the aligned reads having separation distances to adjacent aligned reads that are smaller than a cutoff value. Using alleles from the first group of aligned reads, the method may define a first haplotype or first partial haplotype.

10 Claims, 15 Drawing Sheets

| #CHROM | POS | ID | REF | ALT | QUAL | FILTER | INFO | FORMAT |
|---|---|---|---|---|---|---|---|---|
| 2 | 4370 | rs6057 | G | A | 29 | . | NS=2;DP=13;AF=0.5;DB;H2 | GT:GQ:DP:HQ |
| 2 | 7330 | . | T | A | 3 | q10 | NS=5;DP=12;AF=0.017 | GT:GQ:DP:HQ |
| 2 | 110696 | rs6055 | A | G,T | 67 | PASS | NS=2;DP=10;AF=0.333, 0.667;AA=T;DB | GT:GQ:DP:HQ |
| 2 | 130237 | . | T | . | 47 | . | NS=2;DP=16;AA=T | GT:GQ:DP:HQ |
| 2 | 134567 | microsat1 | GTCT G | GTACT 50 | PASS | NS=2;DP= 9;AA=G | GT:GQ:DP | |

Figure 3B

SEQUENCE LISTING

```
<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aatgatacgg cgaccaccga gatctacac                                      29

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcgtcggcag cgtctgcacc c                                              21

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcgatcgagg acggcagatg tgtataagag acag                                34
```

```
<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
caagcagaag acggcatacg agat                                            24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtctcgtggg ctcggctgtc c                                               21

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caccgtctcc gcctcagatg tgtataagag acag                                 34
```

HAPLOTYPE RESOLVED GENOME SEQUENCING

SEQUENCE LISTING

The instant application contains a Sequence Listing which has been submitted electronically in ASCII format and is hereby incorporated by reference in its entirety. Said ASCII copy, created on Apr. 14, 2014, is named ILMNP005US_SL.txt and is 1694 bytes in size.

BACKGROUND

Most genomic studies to date ignore the diploid nature of the human genome. However, the context in which variation occurs on each individual chromosome can have a significant impact on gene regulation and may have strong clinical significance. Applications that can greatly benefit from phased genomes include medical genetics (e.g. detecting compound heterozygosity); non-invasive fetal genome sequencing, population genetics, cancer genetics, and HLA (Human Leukocyte Antigen) typing and matching. Thus, there is a strong need for cost-effective methods that support accurate and comprehensive haplotype-resolved sequencing of human genomes.

There are two general approaches for genome-wide haplotyping: computational phasing and experimental phasing. Computational approaches to haplotyping, in general, pool information across multiple individuals, preferentially relatives, by using existing pedigree or population-level data. Based on the quality of the reference genomes used, these methods cannot necessarily deliver phasing information across the whole genome. Because the performance of computational phasing is contingent upon multiple parameters including sample size, density of genetic markers, degree of relatedness, sample ethnicity, and allele frequency, its performance for genome-wide phasing will inevitably be limited. Rare and de novo variations, which are medically relevant but not observed at appreciable frequencies at the population level, fail to phase accurately with computational methods.

Most experimental approaches to genome-wide haplotype-resolved sequencing employ sub-haploid complexity reduction, thereby providing a direct and hypothesis-free approach to genome-wide phasing. In vitro implementations of complexity reduction separate the parental copies in compartments through sub-haploid dilution, amplify the individual copies using random primer amplification, and then derive haplotypes by inferring and genotyping the haploid molecules present in each compartment. However, these methods suffer from several limitations. First, random primer amplification-based methods generate false variants through chimeric sequence formation, can result in a biased representation of the genome with allelic drop-out in the diploid context, and can yield underrepresentation of GC-rich sequences. In part as a consequence, very deep sequencing, i.e. 200-500 Gb, is required to obtain phasing information with N50 block sizes in the range of 700 kb to 1 Mb (in which N50 is defined as the phased block length such that blocks of equal or longer lengths cover half the bases of the total phased portion of the genome). Second, the requirement of diluting to sub-haploid content and thus starting with minute amounts of DNA may put a burden on reproducibility, accuracy and uniformity of amplification. The complexity of this step scales linearly with the number of compartments (usually between 96 and 384), in which each compartment represents an individual library preparation from a picogram-scale starting amount. Cloning-based approaches allow working with reasonable amounts of DNA, but require high-efficiency cloning which is time consuming and technically challenging and are also limited to the size of the cloning platform (fosmids/BACs). Finally, for some methods, there is a requirement for upfront size-selection of genomic DNA prior to sub-haploid complexity reduction. Since the reconstruction of long haplotypes is challenging, any limits on the length of input DNA molecules will fundamentally constrain the length of the resulting haplotypes. Alternative approaches for obtaining long-range phasing information include long read technologies, but these currently suffer from low accuracy and throughput. Thus, despite advances in phasing methods, there remain major practical obstacles to their integration with routine human genome sequencing.

SUMMARY

Some aspects of this disclosure concern methods of determining a haplotype or partial haplotype of a DNA sample containing high molecular weight segments of genomic DNA. Such methods may be characterized by the following operations: (a) processing the DNA sample to produce an enriched DNA sample enriched for DNA from a first high molecular weight segment having a plurality of alleles from a first haplotype; (b) sequencing DNA in the enriched DNA sample to produce a plurality of sequence reads, which are shorter in length than the first high molecular weight segment, where some of the sequence reads contain a first allele of the first haplotype and other of the sequence reads contain a second allele of the first haplotype; (c) aligning the sequence reads to a reference genome to produce aligned reads, where aligned reads from the first high molecular weight segment tend to cluster into islands on the reference genome; (d) determining distances separating adjacent ones of the aligned reads on the reference genome, where the separation distances between adjacent aligned reads fall into at least two groups distinguishable by the magnitude of their separation distances; (e) selecting a first group of the aligned reads having separation distances to adjacent aligned reads that are smaller than a cutoff value, thereby excluding aligned reads having greater separation distances, where at least a portion of the first group of the aligned reads belong to the same island on the reference genome; and (f) using alleles from the first group of aligned reads to define a first haplotype or first partial haplotype. Examples of high molecular weight segments include segments that are at least about 50 kb in length on average or at least about 100 kb in length on average. In some embodiments, the methods have an additional operation of determining a complete haplotype from the first partial haplotype and other partial haplotypes.

In certain embodiments, selecting a first group of the aligned reads includes determining the cutoff value. As an example, the determining the cutoff value includes: (i) generating a mixture model from the separation distances between adjacent aligned reads, wherein the mixture model fits two distributions to the separation distances; and (ii) determining the cutoff value from a property of at least one of the two distributions. In some cases, each of the two distributions comprises its own central tendency (e.g., the mean of a Gaussian distribution). In certain embodiments, generating a mixture model involves applying an expectation maximization procedure to the separation distances between adjacent aligned reads.

In some implementations, determining the cutoff value includes an operation of identifying a fraction of the probability mass of the distribution containing the shorter separation distances. For example, the fraction of the probability mass of the distribution containing the shorter separation distances may be about 80% or greater.

Some aspects of the disclosure concern systems for haplotyping genomic DNA samples. Such systems may be characterized by the following elements: (a) a sequencer for receiving nucleic acids samples and providing nucleic acid sequence information from the sample; (b) a processor; and (c) one or more computer-readable storage media having stored thereon instructions for execution on said processor to evaluate sequence reads from the sequencer. The instructions sometimes include the following: (i) aligning the sequence reads to a reference genome to produce aligned reads, wherein aligned reads from a first high molecular weight segment of a genomic DNA sample tend to cluster into islands on the reference genome; (ii) determining distances separating adjacent ones of the aligned reads on the reference genome, wherein the separation distances between adjacent aligned reads fall into at least two groups distinguishable by the magnitude of their separation distances; (iii) selecting a first group of the aligned reads having separation distances to adjacent aligned reads that are smaller than a cutoff value, thereby excluding aligned reads having greater separation distances, wherein at least a portion of the first group of the aligned reads belong to the same island on the reference genome; and (iv) using alleles from the first group of aligned reads to define a first haplotype or first partial haplotype. The instructions may additionally include instruction for carrying out one or more of the above-referenced method operations.

In certain embodiments, the system additionally includes a component configured to process a DNA sample to produce an enriched DNA sample enriched for DNA from the first high molecular weight segment having a plurality of alleles from a first haplotype.

Certain aspects of the disclosure pertain to methods of determining a haplotype or partial haplotype of a DNA sample comprising segments of genomic DNA, where a first segment of the genomic DNA contains sites of a plurality of heterozygous polymorphisms including the site of a first indel polymorphism having first indel allele and a second indel allele. Such methods may be characterized by the following operations: (a) sequencing the DNA sample including the first and second indel alleles (where the sequencing produces a plurality of sequence reads, including at least a first read containing the sequence of the first indel allele and a second read containing the sequence of the second indel allele); (b) examining the sequence reads, including the first read and the second read, to identify and characterize polymorphisms including the first indel polymorphism (where each of the plurality of heterozygous polymorphisms is characterized by a genome location and sequences of each allele); (c) modifying a reference genome to produce two pseudo-reference genomes, a first pseudo-reference genome containing the first indel allele at the genome location of the first heterozygous indel polymorphism, and a second pseudo-reference genome containing the second indel allele at the genome location of the heterozygous indel polymorphism; (d) aligning the first read to the first and second pseudo-reference genomes and determining which of the two pseudo-reference genomes provides the better alignment, and selecting the indel allele of the pseudo-reference genome as belonging to the first segment, (where the first read is from the first segment); and (e) developing a partial or complete haplotype from the alleles of the first segment, where one allele of the haplotype is the indel allele selected in (d). In various embodiments, at least one of the first and second indel alleles is an insertion allele.

In various embodiments, the methods additionally in the following operations: (i) generating a file containing a list of heterozygous polymorphisms in the DNA sample, wherein the list includes the genome location and sequences of each allele of the polymorphisms identified from the sequence reads; and (ii) using the genome location and allele sequences, including sequences of the first and second indel alleles, in the file to prepare the first and second pseudo-reference genomes. As an example, the file is VCF file.

In some implementations, the methods additionally include processing the DNA sample to produce an enriched DNA sample enriched for DNA from the first segment of the genomic DNA, which segment contains a plurality of alleles from a first haplotype including the first indel allele. As an example, the first segment is at least about 50 kb in length or at least about 100 kb. In some cases, sequencing the DNA includes sequencing the enriched DNA sample to produce the plurality of sequence reads, which are shorter in length than the first segment. Some of the sequence reads contain a first indel allele and other of the sequence reads contain a second allele of the first haplotype. In such cases, the methods may include aligning the plurality of sequence reads to the two pseudo-reference genomes to produce aligned reads, where aligned reads from the first segment tend to cluster into islands on the reference genomes. As a further implementation option, the methods may include (i) selecting a group of the aligned reads that belong to a first island on the reference genome; and (ii) using alleles from the group of aligned reads to define the first haplotype or a portion of the first haplotype. In certain embodiments, the methods additional include determining a complete haplotype using the first indel allele and the second allele of the first haplotype.

In some implementations, determining which of the two pseudo-reference genomes provides the better alignment involves comparing scores for alignment of the sequence reads at the genome location of the indel allele.

Some aspects of the disclosure concern systems for haplotyping genomic DNA samples, and the systems may be characterized by the following elements: (a) a sequencer for receiving nucleic acids samples and providing nucleic acid sequence information from the sample; (b) a processor; and (c) one or more computer-readable storage media having stored thereon instructions for execution on said processor to evaluate sequence reads from the sequencer. The instructions include code for performing the following operations: (i) sequencing a DNA sample including first and second indel alleles at the site of a heterozygous indel polymorphism, (where the sequencing produces a plurality of sequence reads, including at least a first read containing the sequence of the first indel allele and a second read containing the sequence of the second indel allele); (ii) examining the sequence reads, including the first read and the second read, to identify and characterize polymorphisms including the first indel polymorphism (where each of the plurality of heterozygous polymorphisms is characterized by a genome location and sequences of each allele); (iii) modifying a reference genome to produce two pseudo-reference genomes, a first pseudo-reference genome containing the first indel allele at the genome location of the heterozygous indel polymorphism, and a second pseudo-reference genome containing the second indel allele at the genome location of the heterozygous indel polymorphism; (iv) aligning the first read to the first and second pseudo-reference genomes and determining which of the two pseudo-reference genomes provides the better alignment, and selecting the indel allele of the pseudo-reference genome as belonging to the first segment (where the first read is from the first segment); and (v) developing a partial or complete haplotype from the alleles of the first segment, wherein one allele of the haplotype is the indel allele selected in (iv). The instructions may additionally include instruction for carrying out one or more of the above-referenced operations for the indel allele processing methods.

These and other features of the disclosure will be presented in greater detail below, with reference to the associated drawings.

BRIEF DESCRIPTION OF THE DRAWINGS

FIG. 3B—This figure presents an example of a VCF file format, containing information about polymorphisms, but not phasing, in a sample.

FIG. 7 discloses SEQ ID NOS 1-6, respectively, in order of appearance.

DETAILED DESCRIPTION

Definitions

Figure 1:
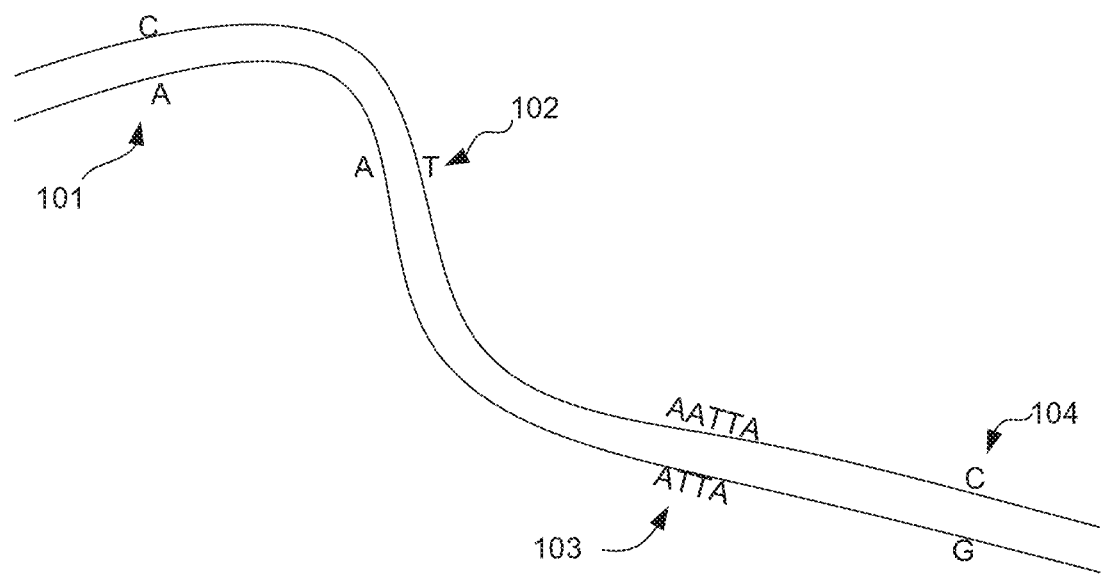
FIG. 1—This figure illustrates a portion of a haplotype in a double stranded nucleic acid segment with 4 polymorphism, 3 SNPs and 1 indel.

Unless otherwise indicated, the practice of the method and system disclosed herein involves conventional techniques and apparatus commonly used in molecular biology, microbiology, protein purification, protein engineering, protein and DNA sequencing, software design and programming, statistics, and recombinant DNA fields, which are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the specification as a whole. It is to be understood that this disclosure is not limited to the particular methodology, protocols, and reagents described, as these may vary, depending upon the context they are used by those of skill in the art.

As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively.

The term "plurality" refers to more than one element. For example, the term is used herein in reference to a number of reads to produce phased island using the methods disclosed herein.

The term "portion" is used herein in reference to the amount of sequence information of genome, chromosome, or haplotype in a biological sample that in sum amount to less than the sequence information of one complete genome, one complete chromosome, or one complete haplotype, as apparent from context.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "biological sample" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

A biological sample can be a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes), transformed cell lines and the like. For example, polynucleotide molecules may be obtained from primary cells, cell lines, freshly isolated cells or tissues, frozen cells or tissues, paraffin embedded cells or tissues, fixed cells or tissues, and/or laser dissected cells or tissues. Biological samples can be obtained from any subject or biological source including, for example, human or non-human animals, including mammals and non-mammals, vertebrates and invertebrates, and may also be any multicellular organism or single-celled organism such as a eukaryotic (including plants and algae) or prokaryotic organism, archaeon, microorganisms (e.g. bacteria, archaea, fungi, protists, viruses), and aquatic plankton.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cfDNA molecules. The term "polynucleotide" includes, without limitation, single- and double-stranded polynucleotide.

The single stranded polynucleotide molecules sequenced by the systems and devices herein can have originated in single-stranded form, as DNA or RNA or have originated in double-stranded DNA (dsDNA) form (e.g. genomic DNA segments, PCR and amplification products and the like). Thus a single stranded polynucleotide may be the sense or antisense strand of a polynucleotide duplex. Methods of preparation of single stranded polynucleotide molecules suitable for use in the described methods using standard techniques are well known in the art. The precise sequence of the primary polynucleotide molecules is generally not material to the disclosed embodiments and may be known or unknown. The single stranded polynucleotide molecules can represent genomic DNA molecules (e.g., human genomic DNA) including both intron and exon sequences (coding sequence), as well as non-coding regulatory sequences such as promoter and enhancer sequences.

The nucleic acid described herein can be of any length suitable for use in the provided methods. For example, the target nucleic acids can be at least 10, at least 20, at least 30, at least 40, at least 50, at least 75, at least 100, at least 150, at least 200, at least 250, at least 500, or at least 1000 kb in length or longer.

The term nucleic acid segment refers to a portion of a chromosome or genome, and in some cases refers to a haploid portion that is sequenced without its complementary strand in order to phase the segment.

The term "site" refers to a unique position (e.g., chromosome ID, chromosome position and orientation) on a reference genome. In some embodiments, a site may be a residue, a sequence tag, or a segment's position on a sequence. The term "locus" may be used to refer to the specific location of a nucleic acid sequence or polymorphism on a reference chromosome.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the non-coding sequences of the DNA.

In various embodiments, the reference sequence is significantly larger than the reads that are aligned to it. For example, it may be at least about 100 times larger, or at least about 1000 times larger, or at least about 10,000 times larger, or at least about 105 times larger, or at least about 106 times larger, or at least about $10^7$ times larger.

In one example, the reference genome sequence is that of a full length human genome. In another example, the reference genome sequence is limited to a specific human chromosome such as chromosome 13. In some embodiments, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species.

In various embodiments, the reference genome is a consensus sequence or other combination derived from multiple individuals. However, in certain applications, the reference sequence may be taken from a particular individual.

The term "polymorphism" or "genetic polymorphism" is used herein in reference to the occurrence in the same population of two or more alleles at one genetic locus. Various forms of polymorphism include single nucleotide polymorphisms, tandem repeats, micro-deletions, insertions, indels, and other polymorphisms.

The term allele refers to one of a number of alternative forms of the same gene or same genetic locus (site). It is the alternative form of a sequence for a character producing different effects. Sometimes different alleles can result in different observable phenotypic traits, such as different pigmentation. However, many genetic variations result in little or no observable variation.

Diploid organisms have one copy of each allele on each chromosome. If both alleles are the same, the polymorphism where the alleles occur is homozygous. If the alleles are different, the polymorphism where the alleles occur is heterozygous. A population of organisms typically includes multiple alleles at each locus among various individuals. Allelic variation at a locus is measurable as the number of alleles present, or the proportion of heterozygotes in the population.

Indel is a term for the insertion and/or the deletion of bases in the DNA of an organism. A microindel is defined as an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The Variant Call Format (VCF) is a specified format of a text file used in for storing genome sequence variations. Existing formats for genetic data such as General feature forma (GFF) store all of the genetic data, much of which is redundant because it will be shared across the genomes of a species. By using the variant call format only the variations need to be stored along with a reference genome.

A "haplotype" is a combination of alleles at adjacent sites on a chromosome that are inherited together. A haplotype may be one locus, several loci, or an entire chromosome depending on the number of recombination events that have occurred between a given set of loci, if any occurred.

A haplotype may include a set of polymorphisms on a single chromosome of a chromosome pair that are associated statistically. Such associations, and the identification of a few alleles of a haplotype sequence, may unambiguously identify all other polymorphic sites in its region. Such information has been investigated for the human species by the International HapMap Project.

Phasing (also referred to as "phased sequencing") refers to obtaining the sequence and/or alleles associated with one chromosome, or portion thereof, of a diploid or polyploid chromosome. Historically, genome sequencing generated a single consensus sequence without distinguishing between variants on separate homologous chromosomes. Phased sequencing addresses this limitation by capturing unique chromosomal content, including mutations that may differ across chromosome copies. In some embodiments, phased sequencing distinguishes between maternally and paternally inherited alleles; this distinction may be useful for understanding disease causality.

In some contexts, phasing may be viewed as the process of identifying the individual complement of homologous chromosomes. Conventional methods for phasing include pedigree analysis, allele-specific PCR, linkage emulsion PCR haplotype analysis, polony PCR, sperm typing, bacterial artificial chromosome cloning, construction of somatic cell hybrids, atomic force microscopy, among others. Haplotype phasing can also be achieved through computational inference methods.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "library" refers to a collection or plurality of nucleic acid template molecules which have a common use or common property such as a common origin; e.g., all members of the library come from a single sample. The members of the library may be processed or modified to so that their membership in the library is clearly identified. For example, all members of a library may share a common sequence at their 5' ends and a common sequence at their 3' ends. Use of the term "library" to refer to a collection or plurality of template molecules should not be taken to imply that the templates making up the library are derived from a particular source, or that the "library" has a particular composition. By way of example, use of the term "library" should not be taken to imply that the individual templates within the library must be of different nucleotide sequence or that the templates be related in terms of sequence and/or source.

The terms "index," "index sequence," "unique identifier," "barcode," and "barcode sequence" are used interchangeably herein unless specified otherwise. The terms refer to a sequence of nucleotides, usually oligonucleotides, that can be used to identify a sequence of interest such as region of a genome or haplotype. The index sequence may be exogenously incorporated into the sequence of interest by ligation, extension, or other methods known in the art. The index sequence may also be endogenous to the sequence of interest, e.g., a segment in the sequence of interest itself may be used as an index. For some implementations of index sequences, see, Kinde, et al. (2011), Proceedings of the National Academy of Sciences, 108, 9530, which is incorporated herein by reference in its entirety.

The term "parameter" herein refers to a numerical value that characterizes a physical property or a representation of that property. In some situations, a parameter numerically characterizes a quantitative data set and/or a numerical relationship between quantitative data sets. For example, the mean and variance of a standard distribution fit to a histogram are parameters.

The term "read" refers to a sequence read from a portion of a nucleic acid sample. Typically, though not necessarily, a read represents a short sequence of contiguous base pairs in the sample. The read may be represented symbolically by the base pair sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

The term "sequence tag" is herein used interchangeably with the term "mapped sequence tag" to refer to a sequence read that has been specifically assigned, i.e., mapped, to a larger sequence, e.g., a reference genome, by alignment. Mapped sequence tags are uniquely mapped to a reference genome, i.e., they are assigned to a single location to the reference genome. Unless otherwise specified, tags that map to the same sequence on a reference sequence are counted once. Tags may be provided as data structures or other assemblages of data. In certain embodiments, a tag contains a read sequence and associated information for that read such as the location of the sequence in the genome, e.g., the position on a chromosome. In certain embodiments, the location is specified for a positive strand orientation. A tag may be defined to provide a limit amount of mismatch in aligning to a reference genome. In some embodiments, tags that can be mapped to more than one location on a reference genome, i.e., tags that do not map uniquely, may not be included in the analysis.

As used herein, the terms "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See International Patent Application No. PCT/US2012/060892 filed Oct. 28, 2012, which is incorporated herein by reference in its entirety. The matching of a sequence read in aligning can be a 100% sequence match or less than 100% (non-perfect match).

The term "mapping" used herein refers to specifically assigning a sequence read to a larger sequence, e.g., a reference genome, by alignment.

The terms "threshold" herein refer to any number that is used as a cutoff to characterize a sample, a nucleic acid, or portion thereof (e.g., a read). The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. Sometimes they are chosen for a particular purpose (e.g., to balance sensitivity and selectivity).

Context for Haplotyping

FIG. 1 depicts a double-stranded nucleic acid segment such as a small segment of a chromosome. The depicted polynucleotide segment is illustrated with four polymorphisms, which are at locations 101, 102, 103, and 104. Locations 101, 102, and 104 contain single nucleotide polymorphisms (SNPs), while location 103 contains an indel (i.e. insertion-deletion) polymorphism, specifically an insertion-type polymorphism. Each set of four alleles on each nucleic acid strand FIG. 1 represents a portion of a haplotype. For example, one haplotype may contain the alleles in the lower single strand depicted in FIG. 1; that is, base A at location 101, base A at location 102, sequence ATTA at location 103, and base G at location 104. Similarly, in this example, another haplotype, one associated with the upper strand shown in FIG. 1, contains base C at location 101, base T at location 102, sequence AATTA at location 103, and base C at location 104. Typically, a haplotype includes a group of two or more alleles inherited from a single-parent. The alleles of a haplotype typically reside on a single chromosome.

Figure 2:
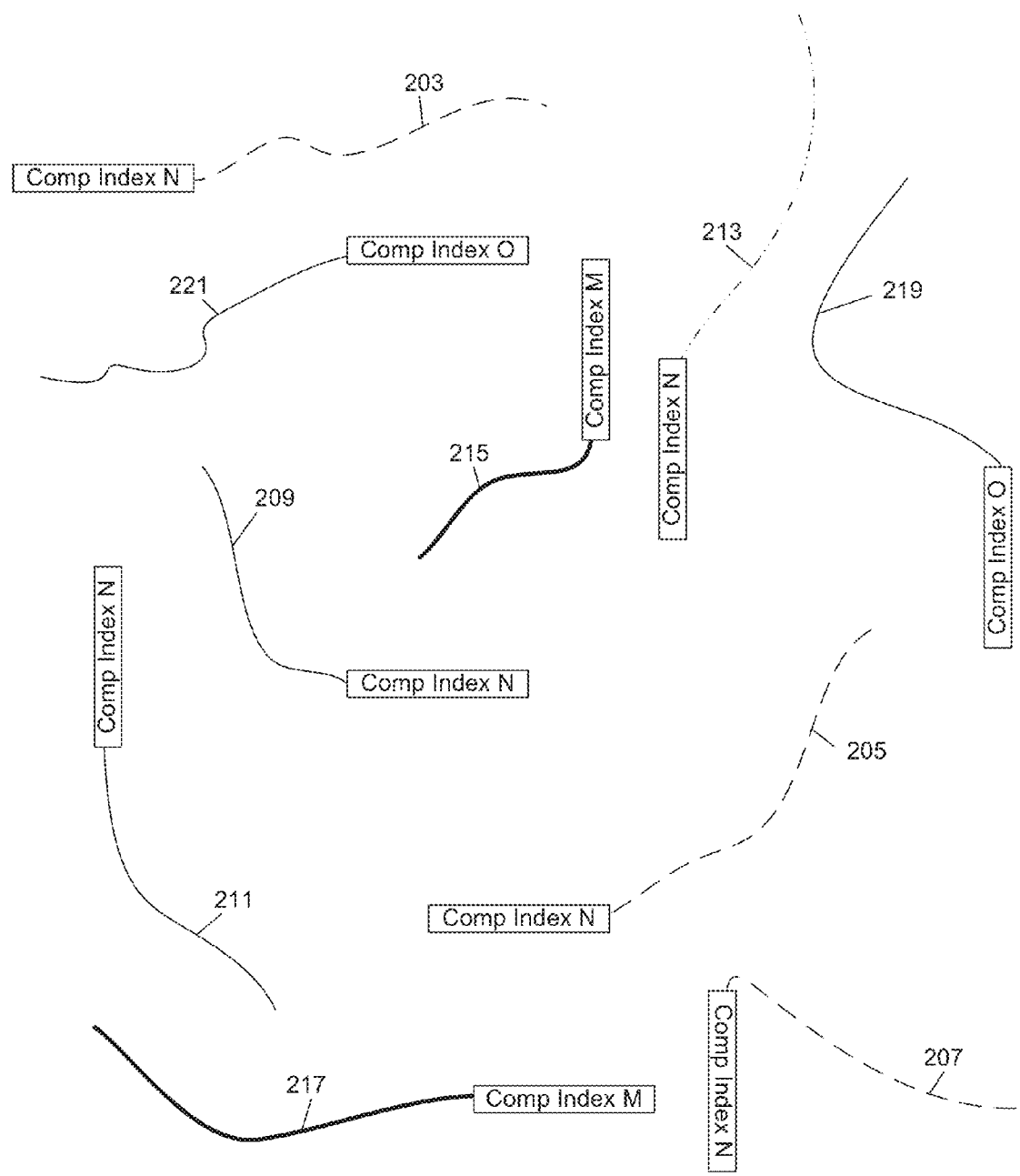
FIG. 2—This figure shows that a particular portion of a haplotype block may be provided with other portions of a haplotype sequence in the same virtual compartment, i.e., sharing the same index. Note that there may be many different ways of providing a sample with haplotype information. Ideally, a single long haplotype could be derived from a single unique index. As a practical matter, it is often more efficient to process multiple DNA sequences originating from different haplotypes in the same virtual compartment, e.g., with the same index.

In certain embodiments, a group of nucleic acid segments having different indexes are processed together. The processing may include applying an adaptor, which may include a portion of the index, amplification primer, etc. For purposes of illustration, assume that multiple nucleic acid segments in FIG. 2 are processed in the same compartment. Further, assume that a subset of the nucleic acid segments belong to the same haplotype. For example, as illustrated in FIG. 2, segments 203, 205, and 207 derive from a nucleic acid segment having alleles from a first haplotype, which is indicated by a dashed curve. Additionally, nucleic acid segments 209 and 211 contain alleles from a second haplotype, which is different from the first haplotype as illustrated by a continuous curve. Note that the segments from the first and second haplotypes share the same index, composite index N. Another segment, segment 213, shares index N but does not derive from the first or second haplotypes. Nucleic acid segments having the same composite index may be said to derive from a single "virtual compartment". The concept of a virtual compartment extends to collections of polynucleotides identifiable by other means (not just composite indexes), but the concept generally denotes a portion of a genome sample containing a substantial fraction of nucleic acid segments originating from a high molecular weight genomic nucleic acid segment that could be processed within the same physical compartment as the rest of the genome, but due to the presence of a unique composite index can be distinguished from the rest of the genome. In some embodiments, the originating nucleic acid has a molecular weight of at least about 100 kb.

In multiplex sequencing implementations, nucleic acid segments having different indexes are sequenced together. For example, all the segments in FIG. 2 may be sequenced together. FIG. 2 depicts a library that contains segments having multiple indexes, M, N, and O. Nucleic acid segments 215 and 217 share the same index, composite index M, and contain alleles from the same haplotype, illustrated by a thick continuous curve. Additionally, nucleic acid segments 219 and 221 share the same index, composite index O, and contain alleles from the same haplotype, illustrated by a dashed/dotted line.

FIG. 2 illustrates an extremely simple collection of nucleic acid segments that may be sequenced together. A real collection will have many more indexed nucleic acid segments, possibly with additional indexes and haplotypes. Sequenced reads can be separated by index. Within the collection of reads from a single index, one or more subsets may derive from one or more haplotypes. Certain embodiments disclosed herein identify groups of contiguous aligned reads having the same phase and frequently deriving from the same haplotype. For example, a process described herein may show that segments 203, 205, and 207 belong to one haplotype block and segments 209 and 211 belong to a different haplotype block, although all segments share the same composite index.

In certain implementations, when all of the nucleic acid segments shown in FIG. 2 are sequenced, and their reads are aligned to a reference genome, some contiguous aligned reads will tend to naturally cluster into distinct islands on the reference genome. The reads in an island may share the same haplotype.

Various techniques may be employed to produce a mixture of indexed nucleic acid segments as depicted in FIG. 2. In certain examples described in this document, such mixture is produced by a tagmentation reaction as described below. In such process and related processes, a single long segment of nucleic acid (e.g., about 50 kb or longer), which may be longer than the length of nucleic acids used in the sequencing reaction, is tagged with a partial index at multiple locations along its length while maintaining its physical contiguity. The long molecule may contain two or more contiguous alleles of a haplotype. In some workflows, the sample is diluted to a point where the tagged long nucleic acid molecules (from paternal and maternal origin chromosomes) can be separated from one another and processed independently. The separation can be achieved either by physical separation or via virtual boundaries established by virtual compartments. In some implementations, the protocol is conducted in a manner ensuring a low probability (e.g., about 3% or less) of having both the maternal and paternal haplotype be present in the same compartment. That is, with very high probability, overlapping reads in the same compartment are generated from the same haplotype, rather than from both maternal and paternal chromosomes.

Some of the high molecular weight nucleic acid segments residing into distinct compartments will contain alleles of partial haplotypes in the original sample. The diluted and separated high molecular weight segments may be fragmented into smaller nucleic acid segments of a size appropriate for sequencing. These smaller segments then may be modified to include the remainder of the index, so that some of the sequence reads sharing the same composite index will be from a region of the genome containing multiple alleles of a haplotype (e.g., reads from segments 203, 205, and 207 in FIG. 2). A tagmentation process as described below provides a good example of a way to implement a method producing a mixture such as shown in FIG. 2. In some embodiments, the sequence reads having a given composite index will belong to a few haplotypes.

Figure 4A:
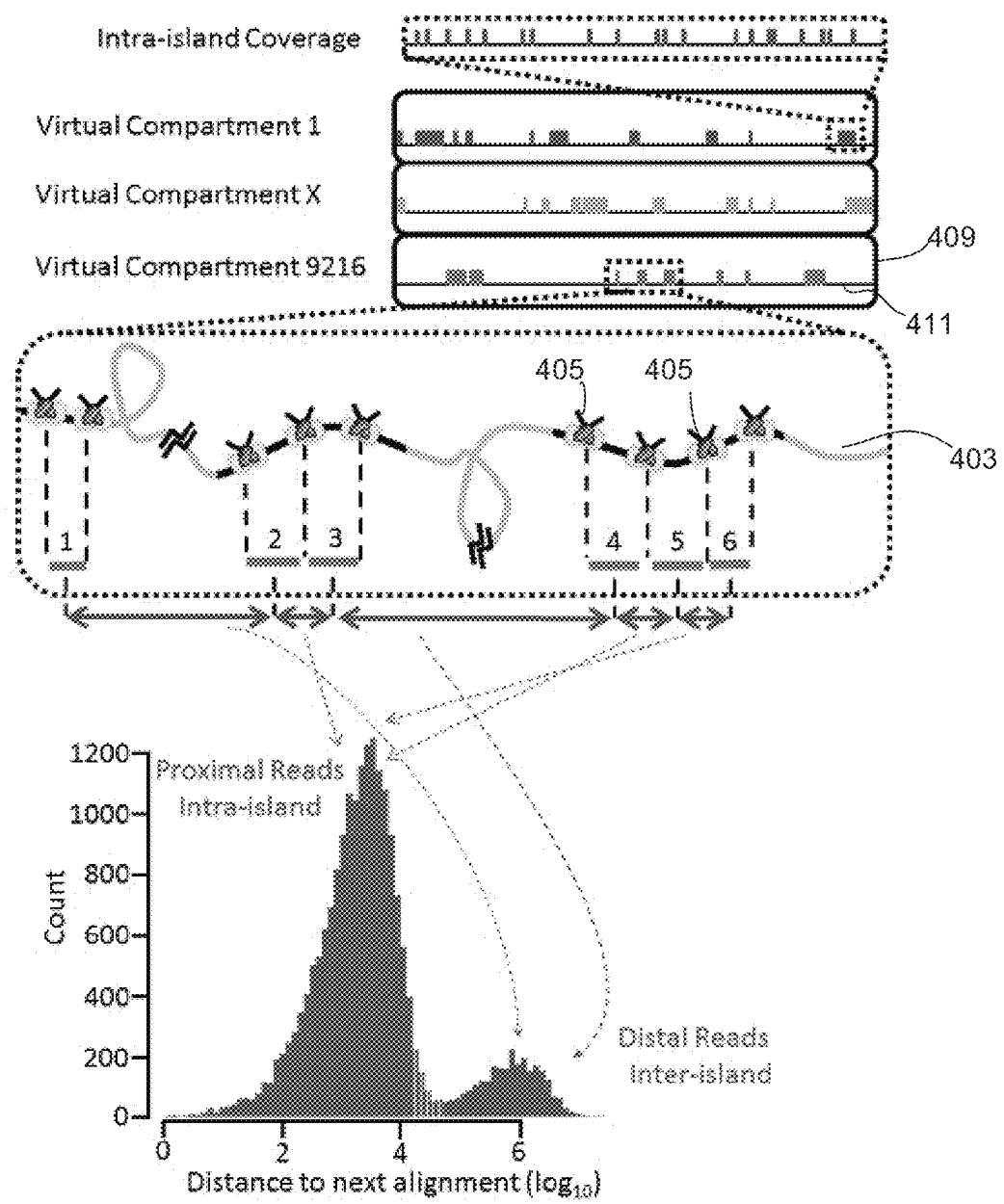
FIG. 4A—This figure illustrates the origin of "islands" of sequence reads derived from the same phase of a chromosome. Specifically, the figure shows a double stranded starting sequence, and an associated distribution of reads (including islands) on a reference genome. Additionally, the figure shows a bimodal distribution of read separation distances with an overlapping area corresponding to lost sensitivity and/or false positives.

FIG. 4A, which is described in detail below, conceptually illustrates certain aspects of a procedure for producing, sequencing, and partially phasing a mixture as illustrated in FIG. 2. As shown in the figure, a long double stranded nucleic acid segment 403 is tagged at various locations along the segment's length. The tags introduce partial indexes for virtual compartments. All nucleic acid segments, including segment 403, in the same physical location are tagged with the same partial index. Other long double stranded segments in other physically discrete locations (not shown) are similarly tagged but with different partial indexes.

As shown, the tagging process applies partial indexes at various locations (e.g., locations 405) along the length of the DNA molecule making up double strand 403 (and other segments in other physical locations), and it does so without fragmenting the long stands, thereby preserving contiguous alleles in the same strand. After tagging, the double strands are denatured and the single stands are physically separated (not shown in FIG. 4A). The physical separation of long single strands, each containing multiple alleles from distinct haplotypes, enables phasing.

The composite indexes are completed by first fragmenting the physically segregated long nucleic acid molecules to produce sequencable single strands containing partial indexes from the tagging process, and then applying the remainder of the index, which represents the unique location where the index is applied (i.e., final compartments). Thus, the composite index includes one portion applied to the long DNA molecule from the original sample, and a second portion applied to segments originating from the same long DNA molecules after they have been separated from their complementary strands in the original genomic sample.

Aligning the reads having the same composite index to a reference genome produces a distribution such as 409 in FIG. 4A, where contiguous reads 4, 5, and 6 align to one region of the reference genome and contiguous reads 2 and 3 align to a different region of the reference genome. Stated another way, aligning reads from multiple DNA sources, some being from highly intact starting gDNA, can produce haplotype islands of strobed reads across long stretches of genomic DNA. See the upper panels of FIG. 4A. The more intact the DNA, the longer the island N50.

It may be noted that a haplotyping assay that uses high molecular weight gDNA can phase effectively across further distances than an assay using lower molecular weight gDNA. Therefore, to the extent possible, it may be desirable to employ high MW segments of gDNA. Long island N50s can be especially useful for studying information-poor regions of the genome, regions containing segmental duplications, or long stretches of homozygosity. A method that utilizes larger DNA segments, e.g., about 100 kb and larger or about 200 kb and larger, ideally as long as intact chromosomes, may deliver more genetic information and genomic context than methods that use size-selected DNA. Additionally, it should be noted that some workflows disclosed herein do not rely on a size selection step, facilitating high throughput.

Computational Pipeline

Figure 3A:
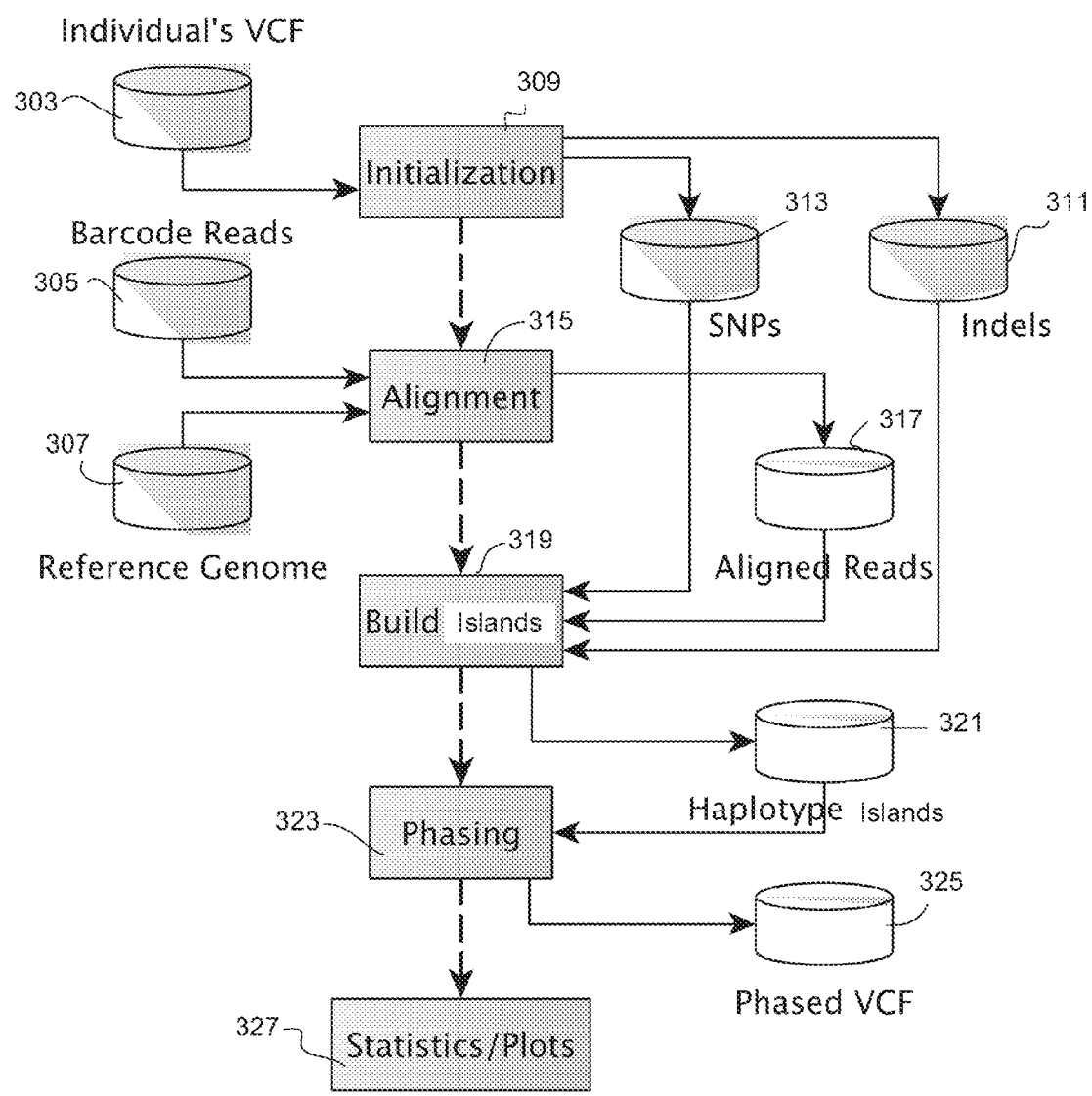
FIG. 3A—This figures presents a flow chart of an example of a data analysis pipeline. In this example, one source of information (VCF files) contains the identity of heterozygous variants in the sample. Another source of data contains aligned reads on a reference genome. In some cases, the aligned reads will all share the same index, but derive from two or more haplotypes.

One example of a computational workflow for assigning alleles to their respective haplotypes is shown in FIG. 3A. The workflow takes sequence reads as input and generates inferred haplotype sequence information from islands of nucleic acid segments (e.g., an island including segments 4, 5, and 6 in FIG. 4A). Ultimately, the workflow provides phased chromosomal sequences as output.

In the embodiment depicted in FIG. 3A, a genomic sample's sequenced reads have a particular index or other defining property that selects for one or more high molecular weight nucleic acid segments, and these reads are analyzed in two ways. First, the reads are processed to identify alleles at discrete polymorphisms. See block 309. Such alleles may be represented as a scaffold, which may be presented in a defined format (e.g., VCF) as depicted in FIG. 3B and shown in block 303. As is known to those of skill in the art, VCF files identify heterozygous and homozygous variant sites (polymorphism sites) from a sample. The locations of many variant sites are known ahead of time, and the alleles from the sample at these sites are recorded in the VCF file. However, if the reads from a sample indicate that there are other variant sites, not previously known, these may be recorded as well in VCF file. The scaffold may provide a complete list of the heterozygous variants, but it does not provide information on how the variants' alleles segregate among the maternal and paternal chromosomes, and hence into phases.

In addition to cataloging alleles at variant sites in, e.g., a VCF file, the process aligns reads to a reference genome as depicted in FIG. 4A upper panels. See block 315 of FIG. 3A. This may be done multiple times, separately for each of multiple indexes or virtual compartments. In some implementations, there are at least about 100 distinct virtual compartments, or at least about 500 distinct virtual compartments, or at least about 1000 distinct virtual compartments, or at least about 5000 distinct virtual compartments, or at least about 10,000 distinct virtual compartments. The aligned reads segregate into groups or islands whose member reads are putatively assigned the same phase; i.e., the grouped reads are assumed to originate from the same single-strand of nucleic acid and therefore potentially harbor multiple alleles of a single haplotype. See block 319.

The method compares the sequence of an island with the alleles at the variant sites provided in the scaffold in the same region of the genome to identify the haplotype alleles in the island. In this way, the workflow ascribes variant alleles of the scaffold to phases. The result is a set of overlapping partially phased chromosome islands that is provided to a phasing algorithm such as ReFHap, which produces a more completely phased chromosome that agrees with the partially phased chromosome islands with minimum conflict. See block 323. The process predicts the underlying haplotypes from the available phased data. In certain embodiments, the predicted haplotypes are provided for sequences having an N50 value at least about 1 Mb. Of course, this length depends on the type of sequencing technology used, depth of sequencing, and quality of input DNA material used, and many other parameters. In various examples, the process improves the phasing from the kb scale to the Mb scale. In certain embodiments, phased islands have average lengths of at least about 20 kb, or at least about 30 kb, or at least about 40 kb, or at least about 50 kb, or at least about 70 kb, or at least about 90 kb, or at least about 100 kb.

From the above discussion, it can be seen that the depicted workflow has three sources of input: (a) a scaffold (e.g., VCF files) of heterozygous variants obtained from whole genome sequencing (see file(s) 303), (b) indexed reads without islands delineated (see file(s) 305), and (c) a reference genome (see file(s) 307). An example of the reference genome is hg19.

As mentioned, the process generates the scaffold from the sequence reads (operation 309), which need not be demultiplexed from multiple virtual compartments. It uses aligned reads and information about known polymorphisms. While not necessary to implement the phasing process herein, such scaffold may be provided in the form of a VCF file. FIG. 3B provides in tabular form a simplified representation of a VCF file. The rows identify each polymorphism known or found in a chromosome from a sample. The two left-most columns uniquely identify the position of the polymorphisms. The fourth and fifth columns identify the reference and alternate alleles, respectively, for the polymorphism.

The heterozygous variant sites from the scaffold are phased with blocks corresponding to the islands. This is accomplished by reading and parsing the scaffold information to identify variants that are heterozygous. See block 309 in FIG. 3A. The resulting list of heterozygous variants includes, for each variant, the two alleles and their position on a chromosome. The alleles may be of any type, e.g., SNPs, microsatellites, indels, etc. The list may be cached as illustrated in files 311 and 313. Particular alleles that match the sequence of the phased islands are selected for inclusion in a haplotype.

Sequence reads 305 and the reference genome 307 serve as input for alignment operation 315. Aligned reads 317 are the output. Note that reads 305 are provided from the same virtual compartment, so they sometimes include multiple adjacent reads of one phase. The aligned reads may be distributed as shown in the example of FIG. 4A.

The aligned reads 317 and heterozygous variants (files 313 and 311) collectively serve as inputs to an island generating routine 319, which places alleles from the variants with phased reads belonging to islands as identified from the alignment. The result is relatively small phased haplotype islands. See files 321.

In some implementations, phasing of haplotyping blocks is conducted without a scaffold of heterozygous variant sites obtained from separate standard whole-genome sequencing. In other words, the method does not employ the scaffold variant information from the VCF files and phases the genome directly from the indexed reads. Such implementations may process the reads to identify heterozygous variants concurrently with island generation. They may be able to avoid whole genome sequencing.

Returning to FIG. 3A, phased island-length haplotyping blocks are further phased (i.e. stitched together) using a phasing algorithm to produce much larger phased sequences and complete haplotypes. See block 323. In some cases, operation 323 assembles overlapping or contiguous islands from multiple indexes (virtual compartments) to predict the haplotype sequences within the region spanned by the overlapping islands, therefore providing larger phased regions within the chromosomes. The predicted haplotype sequences satisfy a requirement of minimum conflict among the overlapping islands. In certain embodiments, this phasing process is conducted by dividing the island data into portions based on their locations on the reference chromosome. For example, the reference chromosome may be split into multiple regions (e.g., three regions), with the reads in each region being processed in parallel. This is done to reduce the execution time of the analysis. Islands widely separated from one another are unlikely to belong to the same haplotype, so little information is lost by divided them into multiple groups based on regions of the chromosome and processing them separately and in parallel.

In phasing operation 323, alleles (SNPs will be used as an example in the following discussion) from all islands are phased using a phasing algorithm such as ReFHap (Duitama, J., et al., *ReFHap: a reliable and fast algorithm for single individual haplotyping.* Proceedings of the First ACM International Conference on Bioinformatics and Computational Biology. Niagara Falls, N.Y., USA, 2010: p. 160-169), incorporated herein by reference in its entirety, HapCUT (University of California San Diego, see Bansal et al., Bioinformatics, v. 24, ECCB 2008, pp i153-i159, incorporated herein by reference in its entirety) or other phasing algorithm. After such phasing, the process optionally removes conflicting SNPs and/or SNPs that are covered by only one data point to improve accuracy, with the tradeoff of reduced coverage. Finally, some of the missing SNPs are optionally imputed using 1000 Genomes (Abecasis, G. R., et al., *A map of human genome variation from population-scale sequencing.* Nature, 2010. 467(7319): p. 1061-73, incorporated herein by reference in its entirety) or other population-level reference genomic variation data. In certain embodiments, imputation is only used as an optional step to fill the gaps for SNPs that are missing from the experimental data, but not for connecting haplotyping blocks. This analysis approach avoids introducing long switch errors and ensures high quality phasing across the genome.

While RefHap and HapCUT phasing algorithms are identified above, the phasing process is not limited to these. Using contiguity information to phase is an NP hard problem that can be solved by brute force algorithms, which may be used but are computationally infeasible for large genomic regions. Other algorithms approximate phasing based on available contiguity information. They are computationally efficient, but provide only an approximation, albeit a good approximation. Examples of algorithms include the HapCUT and ReFHap applications. Examples of other suitable phasing algorithms are described in Eskin et al., *A note on phasing long genomic regions using local haplotype predictions*, J. Bioinform Comput Biol, 2006, v. 4(3), 639-47, and He et al., *Optimal algorithms for haplotype assembly from whole-genome sequence data*, Bioinformatics, 2010, v. 26(12), 183-190, which are incorporated herein by reference in their entireties.

Whole genome phasing may require sequencing beyond 30× coverage (i.e., about 100 Gb for the human genome) which is routinely used for robust variant calling. The percentage of SNPs phased and the accuracy of phasing is a function of sequencing depth; there is an increasing sequencing depth (and consequently cost) requirement associated with higher phasing output and accuracy. Imputation can be used to increase genome-wide coverage of phased SNPs at a lower sequencing depth, but cannot substitute for experimental phasing in the clinical setting where high accuracy may be required. However, with ever lower sequencing cost, the burden will be minimized to a level that every genome can be individually phased for a nominal price.

In some implementations, fast and reliable haplotyping for human genome-wide without imputation can be achieved by sequencing nearly 10,000 "virtual partitions" generated by contiguity preserving transposition and combinatorial indexing, e.g., the tagmentation procedure described below. With as little as 40-60 Gb of sequencing data, a small fraction compared to prior work, nearly all of SNPs (e.g., 96-98%) in individual human genomes can be phased. Haplotyping blocks may be in the megabase range with long switch error rate on the order of about 1-2 per 10 Mb, assuring accurate phasing across the genome. The disclosed method may employ readily available equipment, require minimal hands-on time, and be integrated with, e.g., a microfluidic platform, particularly devices that already utilize combinatorial mixing using nanochannels or electrowetting droplet technologies.

Initial Phasing—Determining Island Boundaries

The following terms are used in this section and should be understood to be distinct: read, fragment, and island. Overlapping reads having the same index or otherwise belonging to the same virtual compartment together define a fragment, which covers the region of a reference genome spanned by the overlapping reads. Neighboring fragments, which are closely spaced and belong to the same virtual compartment, make up an island. Within each island, the constituent fragments are assumed to originate from the same haplotype. In some implementations, the concept of a fragment may not be used.

To the extent that groups of contiguous reads can be ascribed to the same haplotype (i.e., they originate from the same chromosome), they provide a good starting point for generating a partial or complete haplotype. Such groups or islands may be defined from contiguous aligned reads having the same composite index or otherwise originating from the same virtual compartment. The process assumes that each read of an island originates from the same one of the two haplotypes (maternal and paternal) in the region of the island. In the context of FIG. 3A, operation 319 defines the islands. The following discussion presents techniques for identifying islands of aligned reads. As mentioned, such islands may derive from the same haplotype; therefore they share the same phase.

One approach to identifying islands employs distance constraints, which specifies the distance between adjacent reads belonging to a given island. In this approach reads from the same virtual compartment that are separated from adjacent reads by less than a threshold distance are deemed to belong to a single island. The distance is measured in base pairs on the reference genome.

Using the example of FIG. 4A, reads 4, 5, and 6 belong to one island, while reads 2 and 3 belong to a different island. These islands may be identified by the separation distances between reads 4 and 5, between reads 5 and 6, and between reads 2 and 3. The top panel of FIG. 4A presents a view of the two islands. See the dotted rectangular box around a portion of a reference chromosome 411. Similar islands are defined for other virtual compartments as shown in the figure.

In some implementations, the mechanics of island definition include determining a maximum threshold distance between adjacent reads ascribed to a given island. If the distance between adjacent aligned reads is small, it is likely that the reads came from a proximal region of the same molecule of gDNA (i.e., potentially from the same haplotype). However, if the threshold distance is set too small, the island definition sensitivity may be insufficient, and as a consequence the process will produce shorter phased regions. If a threshold distance between reads ascribed to a single island is too large, selectivity suffers and phasing errors are introduced. For example, read 1 in FIG. 4A could be included in the island of reads 2 and 3.

Figure 4B:
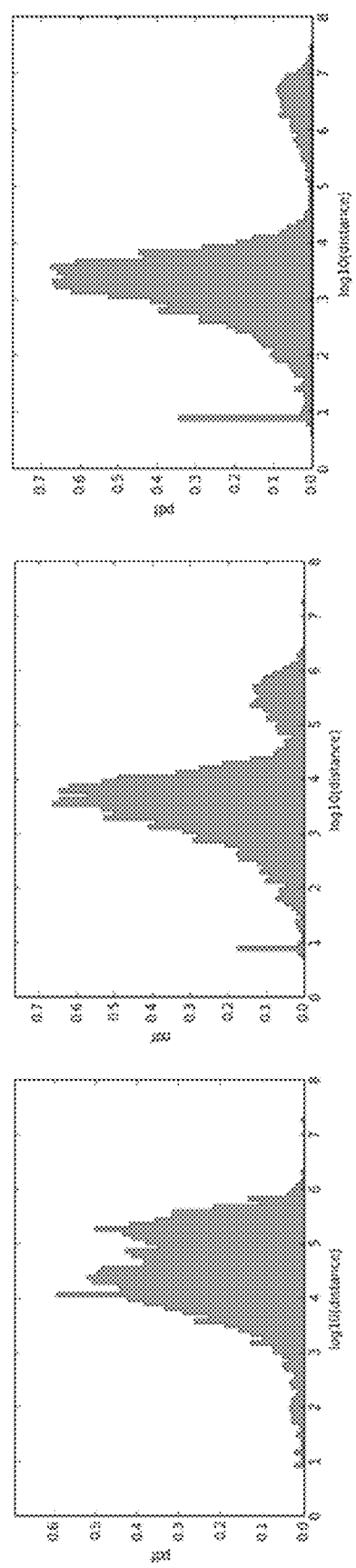
FIG. 4B—This figure shows three actual distributions of read separation distances, taken from different virtual compartments.

As shown in FIG. 4A, bottom panel, the log distances separating adjacent reads on the reference genome can be presented as a histogram having a bimodal distribution, with one mode having many small log separation distances and the other mode having significantly larger log separation distances. Some of the reads represented in the left distribution (small log distances and small mean) share the same haplotype. When the consecutive reads originate from different haplotypes the separation distances fall into the distribution with the larger mean. As can be seen, the modes of the histogram distances have roughly normal distributions. Three actual example histograms are presented in FIG. 4B. Each of these histograms was produced using a composite index and virtual compartment process described elsewhere herein. As can be seen, the features of the bimodal distribution can vary significantly from index to index.

In various implementations, a cutoff threshold is applied to separate the two distributions of read separation distances (which are typically log separation distances). One option involves setting a cutoff definition applicable to all data sets (i.e., an inflexible or fixed setting). An example of such setting defines an island as composed of reads separated from nearest neighbors by less than a threshold distance such as 15 kb). Such an invariant approach may inadequately define islands across many data sets (from different samples, indexes, etc.). A different option choses the cutoff dynamically from the bimodal distribution of adjacent read separation distances in the alignment under consideration. In other words, different thresholds may be determined for reads from different samples or even from different virtual compartments from a single sample.

In the dynamic approach, the procedure may fit data to two ideal distributions, with the left one (smaller separation distances) assumed to identify primarily reads belonging to islands (i.e., reads to which a phase can be ascribed). In certain implementations, the distributions are Gaussians, with each such Gaussian defined by at least a mean and a variance (or standard deviation). Other distributions having a central tendency (mean, mode, median, etc.) can be used.

Figure 4C:
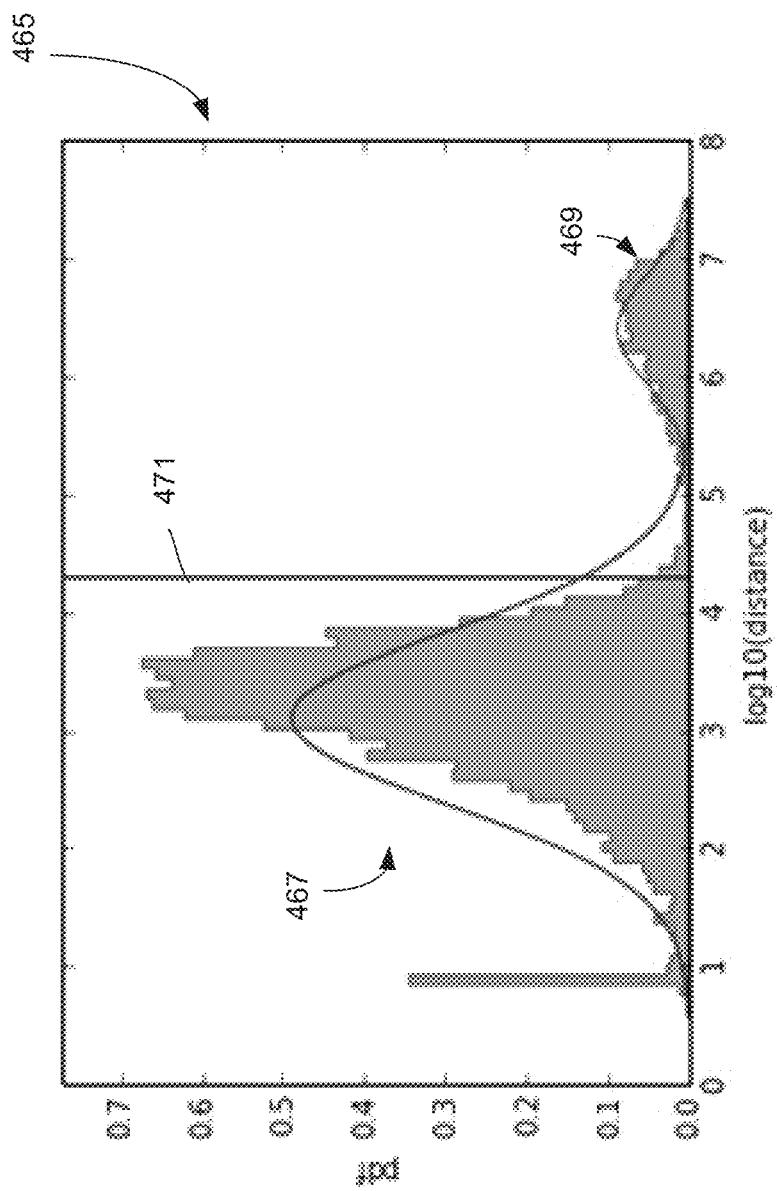
FIG. 4C—This figure shows the bimodal distribution of read distances, as fit to two Gaussians.

FIG. 4C shows an example where two Gaussians (467 and 469) are fit to a bimodal distribution of adjacent read separation distances 465. A cutoff threshold 471 defines a maximum separation distance for island membership. In this example, the cutoff was chosen such that there is 90% probability that adjacent reads are on the same haplotype. It corresponds to read separation distance of approximately 20 kb. Note that the bottom panel of FIG. 4A shows a histogram with two overlapping distributions, where assigning a cutoff in the overlapping region will produce a limited number of false positives and some lost sensitivity.

The two Gaussians (or other ideal distributions) may be identified by any of a variety of techniques. One example uses a mixture model such as a Gaussian Mixture Model (GMM). Certain mixture models fit three parameters: the mean of each Gaussian, the variance of each Gaussian, and the weight of each Gaussian (i.e., the percentage of data belongs to each Gaussian). In this approach, there are three unknowns per Gaussian. The two distributions may be represented as follows:

$$kN_1(\mu_1,\sigma_1)+(k-1)N_2(\mu_2,\sigma_2)$$

where $N_1$ is the left Gaussian, $N_2$ is the right Gaussian, $\sigma$ is the Gaussian variance, $\mu$ is the Gaussian mean, and k is the weight of the left Gaussian.

In one implementation, an Expectation Maximization algorithm fits all these parameters to the data set. An example of a routine that can be used for this purpose includes the "scikit-learn" open source machine learning library built on the SciPy and NumPy computing environments for the Python programming language. However, any method that searches the parameter space for estimation will work. Examples of other methods include a naive grid search and Markov-Chain-Monte-Carlo.

The above-described implementation assumes that there are two components to the mixture and they are both Gaussians. It has been observed that the distribution of these components as Gaussian may not always be the case. For example, the tails of the empirical distributions sometimes contain more probability mass than the inferred Gaussians. (This is sometimes referred to as the heavy tail phenomenon). In order to address this, some implementations employ alternative distributions such the t-distribution.

The method may be designed to find a maximum threshold distance that harbors a certain percentage of the reads in the left distribution (Gaussians or otherwise), e.g., 95% of the probability mass is in the left distribution. As examples, the cutoff threshold may be set such that 70% of the probability mass is in the left Gaussian, or 75% of the probability mass is in the left Gaussian, or 80% of the probability mass is in the left Gaussian, or 85% of the probability mass is in the left Gaussian, or 90% of the probability mass is in the left Gaussian, or 95% of the probability mass is in the left Gaussian.

The threshold distance effectively defines the probability that the distance between two adjacent reads from the same haplotype will be smaller than this threshold. On the other hand, the Gaussian with the larger mean will have a probability mass on the left of the threshold, which defines the specificity of the island definition. Given this balance, the choice of a threshold distance allows flexibility to address particular applications or needs by appropriately balancing sensitivity and specificity. As an example, a threshold of 95% correctly captures 95% of the reads in islands, while 5% of the reads that belong to islands are not captured. The balance may be adjusted as appropriate for applications such as medical genetics (e.g. detecting compound heterozygosity), non-invasive fetal genome sequencing, population genetics, cancer genetics, and HLA (Human Leukocyte Antigen) typing and matching.

Once a threshold is chosen, the process groups the reads fragments having separation distances below the threshold into one or more islands. As mentioned, the entire selection process is part of block 319 in FIG. 3A.

Figure 4D:
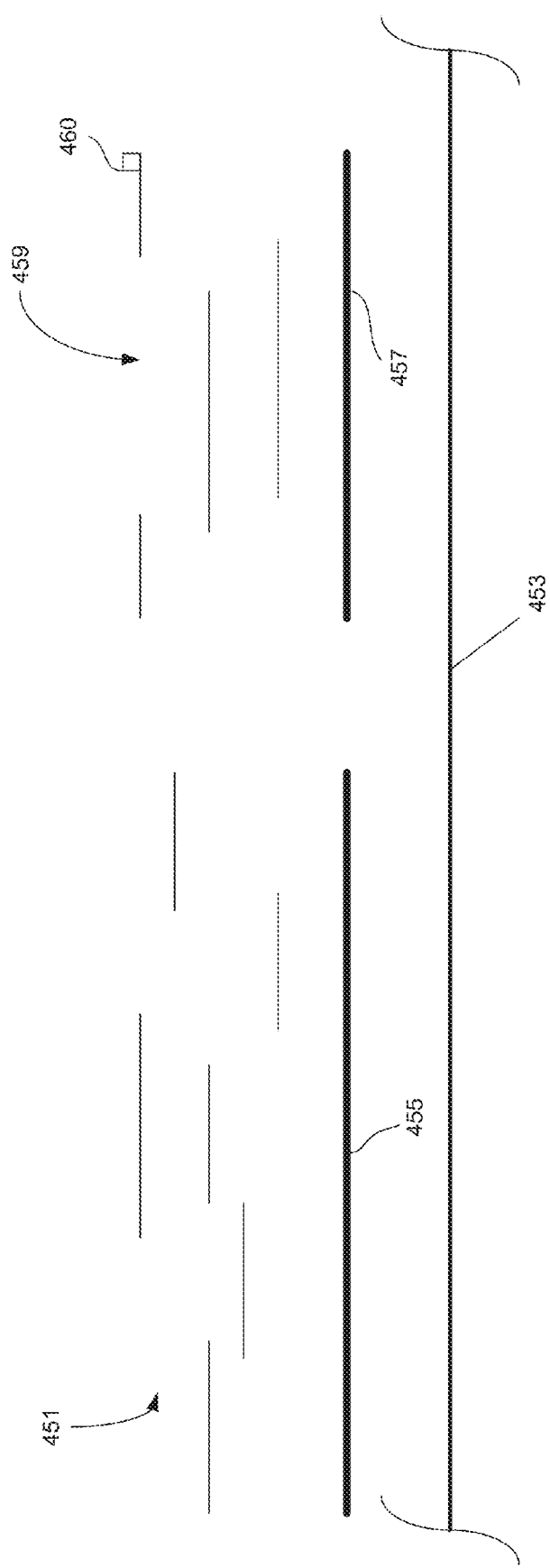
FIG. 4D—This figure illustrates combining overlapping reads into fragments for island definition.

Overlapping reads have a separation of distance of zero. Therefore, it may be convenient to group overlapping reads into fragments and then identify separation distances between the fragments. The genomic region spanned by overlapping reads may be referred to as a fragment. FIG. 4D illustrates overlapping aligned reads within an island. Such distribution may be representative of distributions encountered in actual sequencing of nucleic acid segments from a given virtual compartment. As shown, reads 451 overlap on a region of a reference chromosome 453 and can be combined into a "fragment" 455. Similarly, reads 459 on a different region of reference chromosome 453 can be combined into a fragment 457. In some implementations, a fragment is represented by the smallest start and the largest end coordinate of the overlapping reads on the reference genome. Individual fragments are separated from one another by identifiable separation distances, which the process can use to define islands from fragments generated with reads from a virtual compartment. As an example, the left boundary of fragment 455 and the right boundary of fragment 457 define the end points of an island. In this example, only two fragments make up the island. It is not uncommon to encounter islands made up of three or more fragments.

In certain implementations, the process sorts the fragments with respect to their start positions, where a fragment with a smaller start position (on the reference chromosome) is located on the left of a fragment with a larger start position. Note that the fragments do not overlap; reads that overlap were previously incorporated into fragments. Next the process, determines the distances between all pairs of neighboring fragments (from the same virtual compartment) as the distance between the end position of the left fragment to the start position of the right fragment. Using this arrangement, the process identifies a set of consecutive fragments as islands, where each island has a start position of its left-most fragment and an end position of its right-most fragment.

In certain embodiments, read separation distances, but not fragment separation distances, are used to produce the distributions employed to calculate a cutoff threshold. More specifically, separation distances between non-overlapping reads are used to generate the distributions (e.g., Gaussian distributions). After the cutoff has been determined from the distributions, the cutoff is applied to fragments, rather than reads. Thus, in this embodiment, non-overlapping read separation distances are used to calculate the cutoff, but only fragment separation distances are applied to the cutoff and thereby used to define islands. In some implementations, the process sequence for reads of a single virtual compartment may be described as follows: (a) align reads and determine read separation distances, (b) determine a cutoff threshold from the distribution of read separation distance, (c) generate fragments from the reads, and (d) identify fragments in an island using the cutoff. Of course, the process is repeated for reads from other virtual compartments.

Some processes employ identifiers of the end-position of a high molecular weight DNA segment that originates the island. When the process encounters read having such identifiers, it can process the read (and its associated fragment and/or island) consistent with an understanding that the read comes from the end of the high molecular weight DNA segment.

In some implementations, high molecular weight segments of genomic DNA are labeled with unique end markers before completing the processing in virtual compartments (e.g., before one or of the following steps: applying partial indexes with transposase fragmenting the high MW segments, diluting the segments, physically separating them, completing the indexes, etc.), In certain embodiments, the end-markers are applied to the DNA segments by ligation of adapters having the end marker sequence, or by long range PCR or whole genome amplification with primers that have the end marker. For illustration, FIG. 4D shows one read, of the group of reads 459, labelled with an end marker 460. Typically, a single end marker sequence is applied to all high MW DNA segments. When the reads are processed, the system detects end marker sequences and concludes that the read having the sequence is at the end of one of the original high MW DNA segments. This allows the system to recognize potentially mistaken mergers of two or more smaller islands into a larger island. Such merger could occur because there may be a chance, typically a small chance, that a virtual compartment contains both maternal and paternal haploid DNA from proximal or overlapping regions of the genome. If the system detects that any putative island has an end-marker in the middle of it, it will recognize that, the island has to be broken to two, and then apply an island end point at the site on the genome where end-marker is found. This improves the phasing accuracy.

As indicated, all fragments of an island are presumed to be in phase. This provides phase information on not just the fragments but on larger genomic regions spanned by the islands. A goal of the computational pipeline is to achieve long phased genomic regions with high accuracy. One way to provide both long regions and high accuracy is to include as many haplotype sharing fragments as possible in the same island.

Figure 4E:
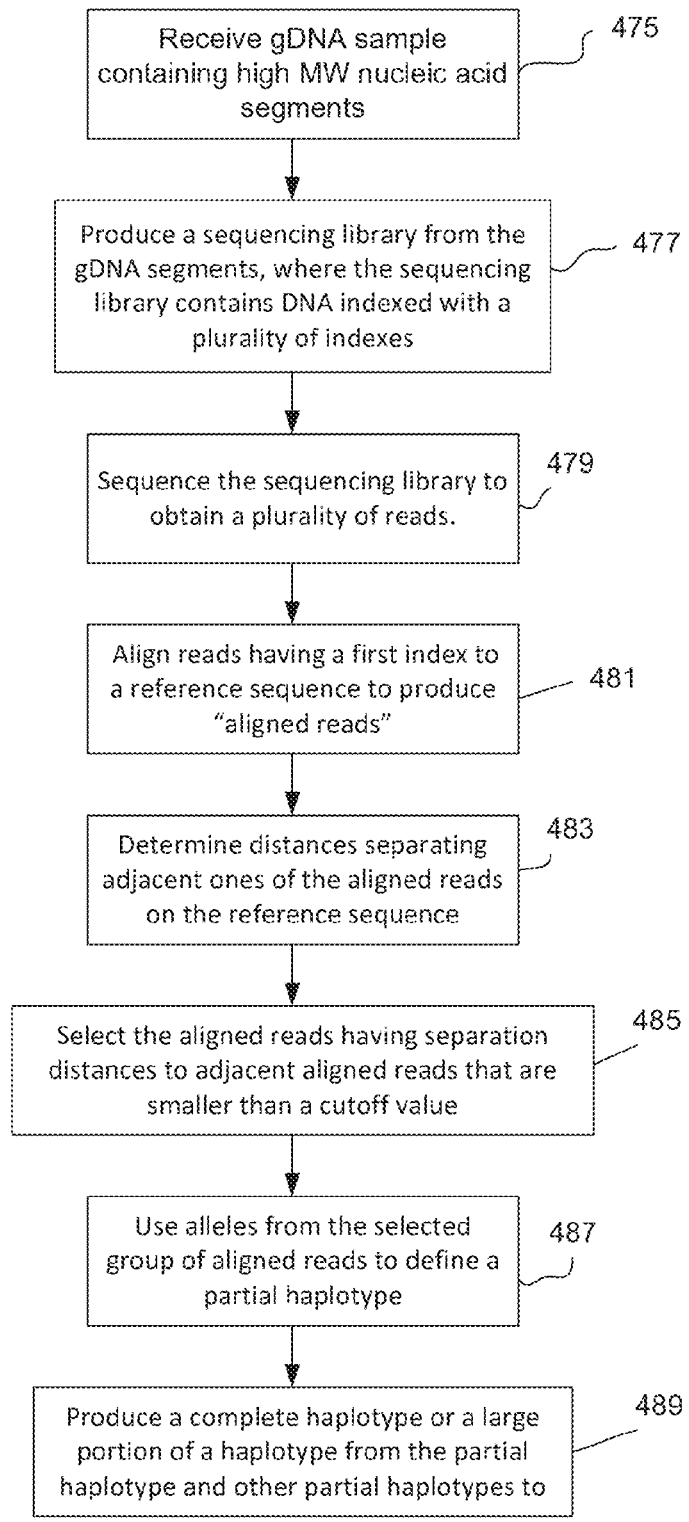
FIG. 4E—This figure presents a flow chart of the island separation process.

FIG. 4E presents a flow chart of an example haplotyping process that employs phased islands produced as described herein. As shown, the process begins at an operation 475 with a genomic nucleic acid sample containing relatively large nucleic acid segments (e.g., about 100 kb or larger), where at least one of the nucleic segments contains two or more alleles of a haplotype.

Next, in an operation 477, the process produces a sequencing library from the genomic nucleic acid segments, where the sequencing library contains smaller polynucleotides indexed with a plurality of indexes (at least one of them common to multiple reads from a single stand of a large nucleic acid segment). A first subset of the polynucleotides sharing a first index was obtained from at least one nucleic acid segment containing two or more alleles of a haplotype. Different indexed polynucleotides of the first subset contain different alleles of the haplotype, but do not contain alleles from outside the haplotype.

Next, in an operation 479, the process sequences the sequencing library to obtain a plurality of reads. Then, in an operation 481, the process aligns reads having the first index to a reference sequence, where the aligning produces aligned reads on the reference sequence, which the process examines to determine distances separating adjacent reads on the reference sequence, where the separation distances between adjacent aligned reads fall into at least two groups distinguishable by the magnitude of their separation distances. See operation 483.

Next, in an operation 485, the process applies a dynamically determined separation distance threshold to select adjacent aligned reads or fragments separated by distances smaller than the threshold, thereby excluding a group having large separation distances. The reads or fragments having separation distances less than the threshold are grouped in an island. Thereafter, the process uses alleles from the reads of the island to define a partial haplotype. See operation 487. Finally, the process uses the partial haplotype and other partial haplotypes to produce a complete haplotype or a large portion of a haplotype. See operation 489. It should be understood that the process applied to phase an island or islands from a single virtual compartment is performed repeatedly with reads from other virtual compartments of the sample. Thus, as an example, the process may be repeated about 10,000 times.

Initial Phasing—Aligning Indels and Inersertions

When a polymorphism is an indel, e.g., insertion or deletion with respect to the reference genome, a challenge is faced in that the same indel may be represented multiple ways; for example it may be aligned multiple different ways to a generic reference sequence. As one example, suppose a reference genome represents a sequence near an allele as AATAA, while a read contains AAA at the allele location.

Reference—AATAA

Read—AAA

In some contexts, the read could be interpreted as having a deletion of T after the second A (e.g., AA-A). But there are other options. For example, the read also could be interpreted as having a deletion of T after the first A (e.g., A-AA). Depending on how indel alleles are presented in the VCF file, they might not match how an aligner aligns indel-containing reads to the reference sequence. There is no one way to represent the indel. Thus, at some levels of analysis, an indel event can be represented in different ways, and as a consequence, different aligners may map indel-containing reads differently.

Some heterozygous indel polymorphisms have alleles of different lengths, which further complicates the problem. The aligner does not know, a priori, how many bases are inserted or deleted in the read it is considering. As a further example, a read containing the sequence AATATTTAA may be aligned to a reference sequence AATAA in multiple ways depending on the parameters employed by the aligner. One alignment may identify an insertion as TTT (AATATTTAA), while another alignment may identify and insertion as TATT (AATATTTAA). Aligning SNP-containing reads does not suffer from this difficulty as SNPs have only one variable position.

Indels present a further complication in that calling them is noisy. The quality of the alignment depends on the number and quality of reads obtained at the location of the indel.

In certain disclosed embodiments, alignment employs a mechanism to provide indel information in the VCF file and indel information used by the aligner in the same format. Ideally, the two information sources have the same representation scheme. As explained, VCF files identify polymorphisms, including indels, by providing a location on a chromosome where the heterozygous indel resides and both alleles at the location. For example, the file may specify that on chromosome 1, position 1000, indel alleles ACA and ATTT exist in the sample under consideration.

In certain embodiments, a phasing system uses polymorphism information from a VCF file to create two different reference genomes on the fly, one for each indel allele. Starting with a base reference sequence that does not clearly specify an indel, a system creates a first pseudo-reference sequence having one indel allele at the location of the polymorphism and a second pseudo-reference sequence having the other indel allele at the location of the polymorphism. This is illustrated in FIG. 5B. Thus, for the example in which the indel alleles are ACA and ATTT, the system might create the following two pseudo-reference sequences:

. . . AAT*ACA*AA . . .

. . . AAT*ATTT*AA . . .

Using the two pseudo-reference sequences, the system aligns the reads again to provide a more robust means of aligning reads containing indels. The system aligns each read to each pseudo-reference sequence, and compares the results to determine which alignment better maps the reads and thereby determines which indel is present in the reads and consequently which indel is in an island containing the read. As explained above, the multiple reads of an island may be identifiable by, e.g., sharing the same index and being closely spaced on the reference sequence.

Figure 5A:
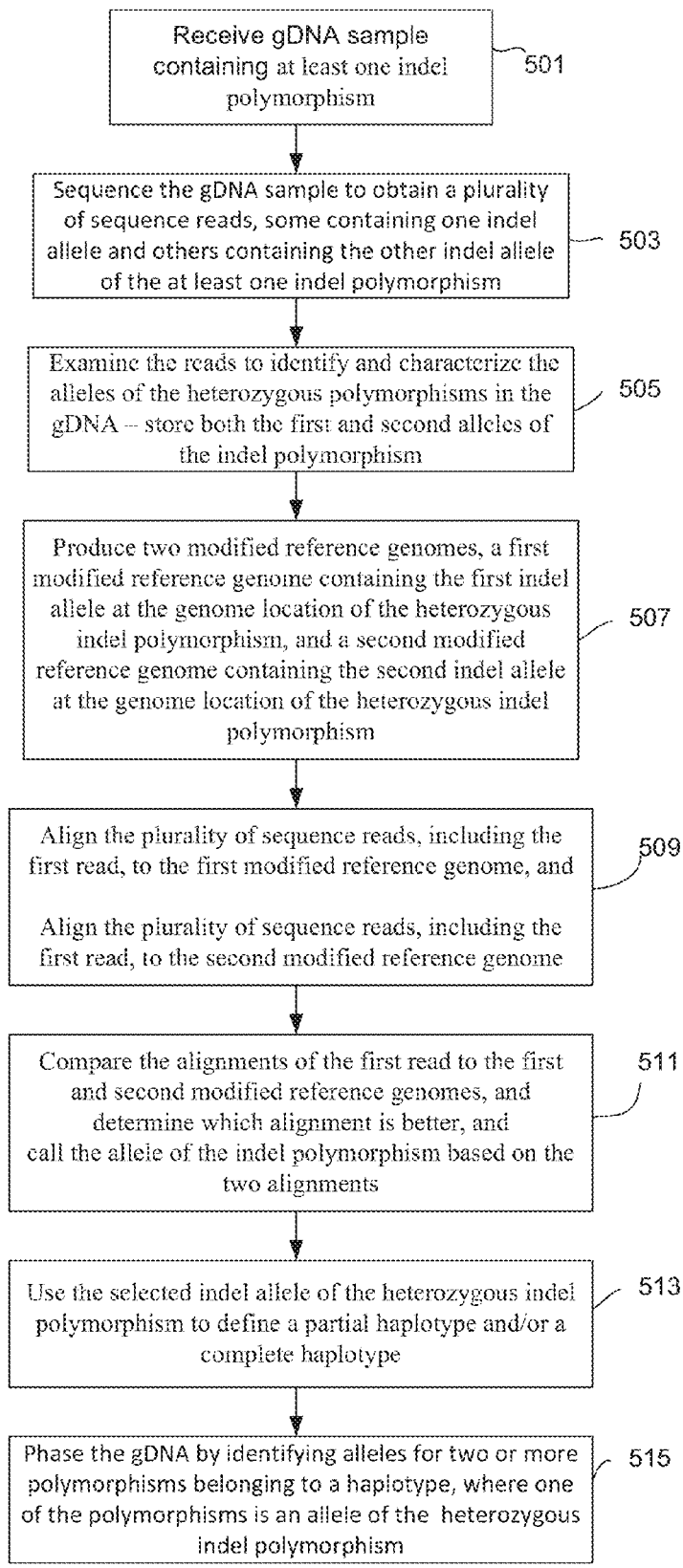
FIG. 5A—This figure is a flow chart of a phasing process having specialized indel processing.
Figure 5B:
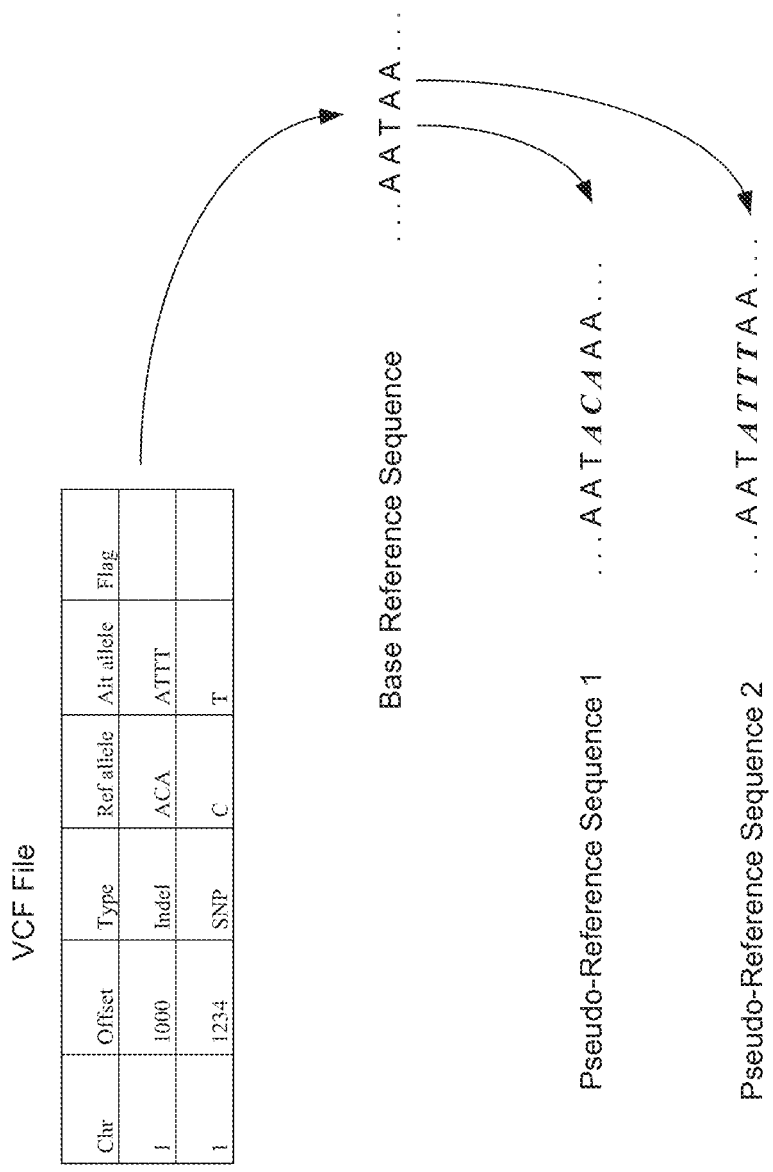
FIG. 5B—This is a related figure showing how two separate derivative reference genomes are generated from the two indel alleles identified in the VCF file or other source.

An example process employing an indel alignment scheme will now be presented with reference to FIGS. 5A and 5B. The process begins with a nucleic acid sample from a genome. See block 501 of FIG. 5A. The sample contains heterozygous polymorphisms including at least one indel polymorphism containing two alleles, each having a different insertion and/or deletion sequence.

Next, as illustrated in block 503, the process sequences the nucleic acid sample including both alleles of the heterozygous indel polymorphism to produce a plurality of sequence reads, including at least a first read containing one indel allele of the heterozygous indel polymorphism and at least a second read containing the other indel allele of the heterozygous indel polymorphism. Next the process examines the reads, including the first and second reads, to identify and characterize each allele of each of a plurality of heterozygous polymorphisms in the genomic nucleic acid sample. See block 505.

The heterozygous indel polymorphism is characterized by a genome (or chromosome) location and a first sequence specifying the first indel allele sequence and a second sequence specifying the second indel allele sequence. In certain embodiments, this information is provided with similar information on other polymorphisms found in the sample. Such information may be included in a VCF file, as described above.

As explained, a sequence read containing an allele of the indel polymorphism may be aligned to a generic reference genome in two or more ways depending on the algorithm used by the aligner. In other words, there may be ambiguity in the alignment of a read containing an indel allele to a reference sequence that does not contain the indel allele. To address this, the process modifies a reference genome to produce two pseudo-reference genomes, a first pseudo-reference genome containing the one indel allele at the genome location of the heterozygous indel polymorphism, and a second pseudo-reference genome containing the other indel allele at the genome location of the heterozygous indel polymorphism. See operation 507 and FIG. 5B.

The process may handle multiple indel polymorphisms in various ways. For example, it may use VCF file labels that flag observed heterozygous indel as 0/1, meaning the reference genome/and the alternate that is observed in the sample. Some polymorphism may contain two non-reference alternate alleles, 1/2, which can also be designated 0/1 for simplicity, so in either case the labeling is binary. In certain embodiments, all the 0-labeled indels are incorporated into one pseudo-reference genome and all the 1-labeled indels are incorporated into the other pseudo-reference genome.

At this point, the process aligns the plurality of sequence reads, including the first read, to first pseudo-reference genome. It also aligns the plurality of sequence reads, including the first read, to second pseudo-reference genome. See operation 509. The process then compares the alignments of the first read to the first and second pseudo-reference genomes, and determines which alignment is better. From this, the process calls the indel allele. See operation 511. In certain embodiments, the indel-containing read alignments are scored for both of the pseudo-reference genomes and the genome providing the higher scoring alignment is selected. In some implementations, a minimum mapping score is specified, and if neither alignment exceeds this score, the process does not report a call for the indel in question. Additionally, some embodiments specify a minimum required overlap of the read and the indel sequence in the pseudo-reference genome to which the read is aligned. For example, a no call will result unless the read covers the indel site with at least the minimum overlap value of bases in the flanking region.

Multiple reads may cover an indel site within an island fragment. From each read, a call is reported if the applicable minimum requirements are satisfied. Then, from all the overlapping reads, the process chooses the indel allele that represents the majority of the calls. Often, there is a single consensus.

From the aligned indel allele of the heterozygous indel polymorphism, the process defines a partial haplotype and/or a complete haplotype. See operation 513. It does this by identifying alleles for two or more polymorphisms belonging to a haplotype, where one of the polymorphisms is the selected heterozygous indel polymorphism. At this point, if appropriate, the process may use a partial haplotype, including the indel allele identified in operation 511, to further phase the genomic nucleic acid. See operation 515. This additional phasing may correspond to operation 323 of FIG. 3A.

The phasing of the indels may be accomplished indirectly through the phased SNPs. In each island, the phased SNP information and the indel calls are available. The process resolves the indel allele to haplotype assignment by comparing the majority of the alleles paired with their closest phased SNPs.

Example Methodology for Producing Indexed Segments Preserving Contiguity

One approach for genome-wide haplotyping based on contiguity preserving transposition and combinatorial indexing employs virtual compartments as described in this section. In certain embodiments, the method begins with Tn5 transposition of undiluted, high molecular weight DNA molecules introducing specific adapter and index sequences at high frequency, while preserving the contiguity and ordering information of the target DNA. After dilution and compartmentalization, the transposase is removed, resolving the DNA into an indexed, fragmented library. The DNA content of each compartment, enriched for neighboring genomic elements, is then indexed at an additional level via PCR. The combinatorial (e.g., 96-plex) indexing at both the transposition and PCR stage subsequently enables the assignment of individual sequencing reads to one of many (e.g., nearly 10,000) virtual compartments. An example of this process is presented in PCT Patent Application PCT/US2013/031023, filed Mar. 13, 2013 titled Methods and Compositions for Nucleic Acid Sequencing, which is incorporated herein by reference in its entirety. Phased synthetic reads constructed from each virtual compartment can be as long as the physical length of input DNA.

An example of a procedure for generating a virtual compartment enriched for neighboring nucleic acid segments from a single maternal or paternal chromosome will now be described. In certain embodiments, a hyperactive version of the Tn5 transposome is employed to simultaneously fragment DNA and introduce adaptors at high-frequency (100-300 bp intervals) in vitro, creating sequencing libraries for next generation DNA sequencing. See Caruccio, N., *Preparation of next-generation sequencing libraries using Nextera technology: simultaneous DNA fragmentation and adaptor tagging by in vitro transposition*. Methods Mol Biol, 2011. 733: p. 241-55; and Adey, A., et al., *Rapid, low-input, low-bias construction of shotgun fragment libraries by high-density in vitro transposition*. Genome Biol, 2010. 11(12): p. R119, both incorporated herein by reference in their entireties. This protocol could remove any phasing or contiguity information due to the fragmentation of the DNA. However, the Tn5 transposase enzyme stays bound to its DNA substrate post-transposition (FIG. 4A), and the protein-DNA complex only dissociates after removal of transposase by the addition of a protein denaturing agent such as SDS (Sodium Dodecyl Sulfate)). Each transposed DNA molecule retains its contiguity and high molecular weight, and is only fragmented when exposed to SDS or other agent causing transposase removal. Transposed DNA undergoes fragmentation upon treatment with a protease, an alternative to SDS, which digests the transposase. Tn5 can be used for inserting custom-designed oligonucleotide sequences into target DNA while maintaining order and extensive contiguity of the original substrate DNA.

Figure 6:
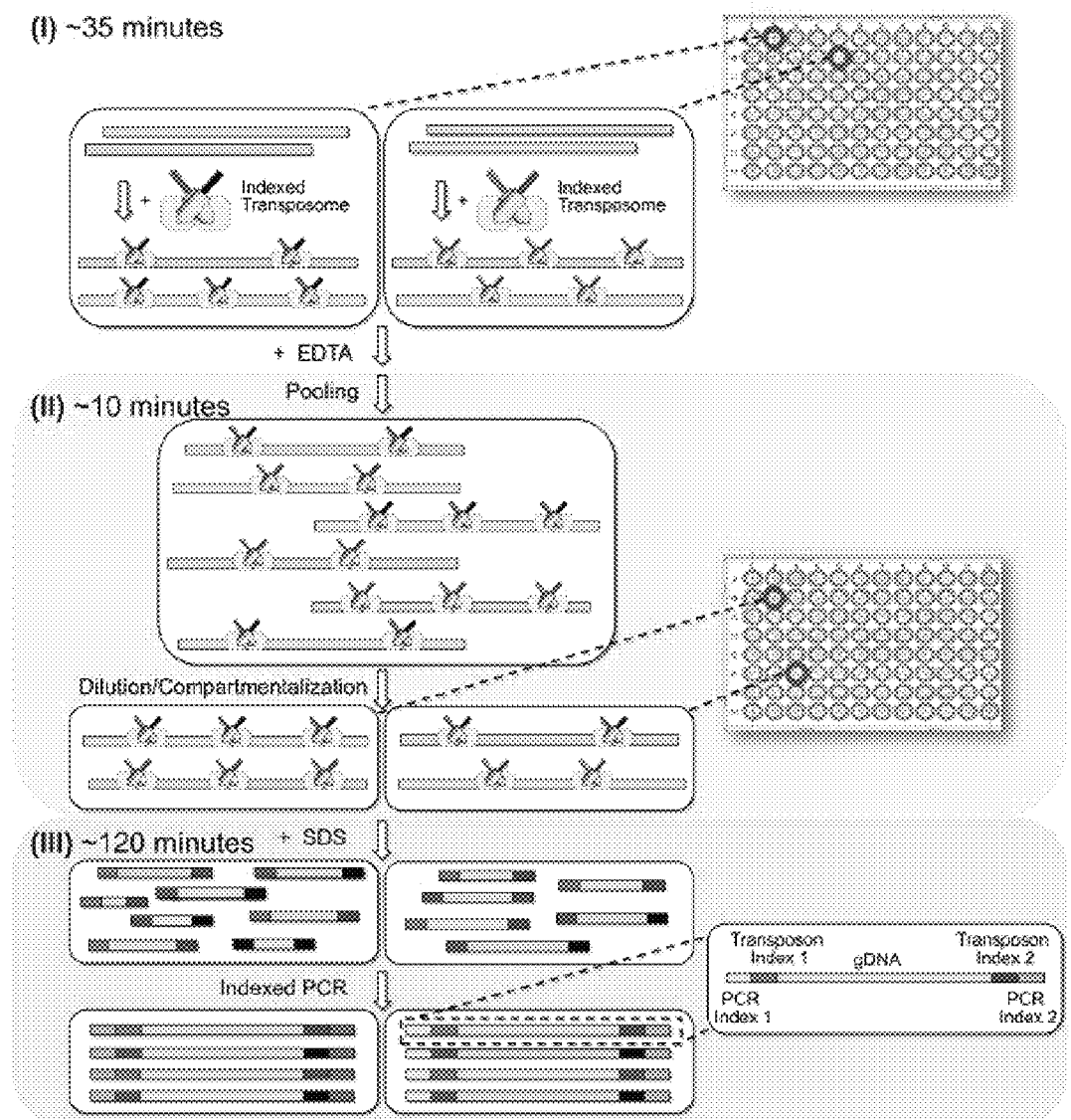
FIG. 6—This figure depicts the use of virtual compartments for enriching neighboring DNA segments from the same maternal or paternal chromosome. The virtual compartments are created from multiple virtual partitions within each of multiple physical compartments, using a combinatorial two-step indexing scheme.

Effective dilution haplotyping may employ sub-haploid dilution of the contiguity-preserved genomic library into multiple compartments followed by indexed PCR. To minimize the number of physical compartments required and to economize on reagents, the process may use virtual compartments, e.g., virtual partitions within each physical compartment, using a combinatorial two-step indexing scheme such as that illustrated in FIG. 6. The first index is incorporated into the gDNA library during transposition (defining the virtual partitions) and the second index is incorporated during indexed PCR of the physical compartment. In this manner, a set of virtual partitions, equal to the number of indexed transposition reactions in the first step, can be defined within a set of physical compartments.

As an example, within each physical compartment, a set of M "virtual partitions" can be created from a single genomic sample by splitting the sample into M independent transposition reactions, each with a unique index incorporated during transposition (using indexed adaptors loaded onto the Tn5 transposase). These separately indexed genomic libraries (contiguity preserved), are then pooled, diluted, and pipetted into a set of N discrete physical compartments, with each physical compartment now having M partitions (i.e., virtual partitions). A second index is incorporated during indexed PCR of the physical compartment. The total number of "virtual compartments" for analysis is M×N.

One example implementation of this concept includes taking a gDNA sample and aliquoting 1 ng into 96 different wells of a microtiter plate, each well containing a Tn5 transposome mix with a unique index (M=96; "virtual partitions"). After tagmentation, the 96 indexed genomic libraries (contiguity preserved) are pooled, diluted, and once again compartmentalized by distributing the diluted pool into 96 separate wells of a microtiter plate (N=96; "physical compartments"). The original pool may be diluted such that there is approximately 3% haploid content per virtual partition or ~3 copies of genome per physical compartment (e.g., 96 virtual partitions in each of the 96 physical compartments). Such low haploid content per virtual compartment helps avoid collisions between maternal and paternal copies from the same genomic region, but the extent of dilution required per physical compartment is two orders of magnitude (e.g., 96-fold) less than other haplotyping approaches that utilize sub-haploid complexity reduction.

After physical compartmentalization, the DNA-transpososome complexes are denatured by SDS (or other agent that fragments the complexes), and the content of each compartment is amplified with a pair of indexed PCR primers (e.g., 96 different PCR indexes). This two-step indexing process effectively creates M×N=96×96=9216 "virtual compartments". In some embodiments, both the first and second indexes are introduced using an asymmetric library adapter (such used in the sequencing technology of Illumina, Inc. of San Diego, Calif.) that contains both the index and universal P5 and P7 primers on both ends of a sequencing template. In this way, the two-level indexing may create a set of 96×96=9216 uniquely indexed partitions (virtual compartments) by using only 8+12 oligonucleotides for making 96 indexed transposomes and 8+12 oligonucleotides for making 96 indexed PCR primers, for a total of 40 unique oligonucleotides. After PCR, indexed libraries from all wells are combined and sequenced using, e.g., a dual indexing workflow to read the four indexes (two pairs, each having a transposition and PCR-level index) and genomic DNA inserts. See FIG. 6. In summary, genome-wide haplotype information can be captured with a simple workflow includes three steps: (I) parallelized and indexed transposition of HMW genomic DNA, (II) pooling, dilution, and physical compartmentalization of transposed libraries, and (III) parallelized and indexed PCR.

Figure 7:
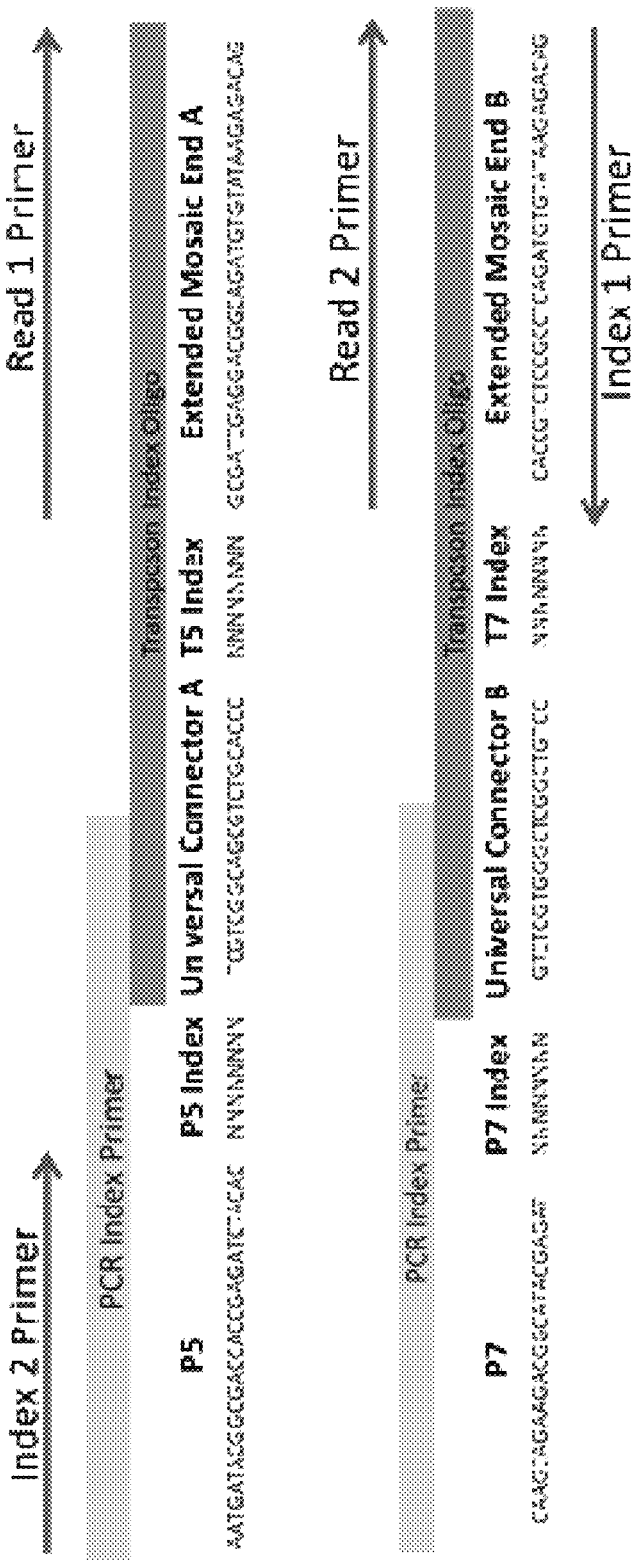
FIG. 7—This figure depicts a process using virtual compartments, e.g., virtual partitions within each physical compartment, using a combinatorial two-step indexing scheme such as that illustrated in FIG. 6.

FIG. 7 depicts the design of two-level (transposon and PCR) indexed templates and sequencing readout scheme. Universal transposon sequences and indexes (i.e. T5 and T7 index) are introduced to the sample during the transposition step. During the PCR step, the overlap between the PCR and transposon oligonucleotides (i.e. Universal Connector) is used to introduce universal sequencing primers (i.e. P5 and P7) together with the PCR index (i.e. P5 and P7 index).

Sequencing Methods

As indicated above, the nucleic acid samples are sequenced as part of the phasing procedure. Any of a number of sequencing technologies can be utilized.

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In one illustrative, but non-limiting, embodiment, the methods described herein comprise obtaining sequence information for the nucleic acids in a sample, e.g., gDNA in a sample, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm2. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting embodiment, the methods described herein comprise obtaining sequence information for the nucleic acids in the sample from a subject being screened, and the like, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein comprises obtaining sequence information for the nucleic acids in the sample from a subject using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting, embodiment, the methods described herein comprise obtaining sequence information for the nucleic acids in the sample from a subject using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector comprises a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting embodiment, the methods described herein comprise obtaining sequence information for the nucleic acids in the sample from a subject using nanopore sequencing (e.g. as described in Soni GV and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein comprises obtaining sequence information for the nucleic acids in the sample from a subject using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the present method comprises obtaining sequence information for the nucleic acids in the sample using the Halcyon Molecular's technology, which uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers to extract base sequence information from the DNA. The method is further described in PCT patent publication WO 2009/046445. The method allows for sequencing complete human genomes in less than ten minutes.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method comprises obtaining sequence information for the nucleic acids in the sample using sequencing by hybridization. Sequencing-by-hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In another embodiment, the present method comprises obtaining sequence information for the nucleic acids in the sample by massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA, e.g., cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA, e.g., cfDNA, is amplified using PCR before it is subjected to cluster amplification. Alternatively, an amplification-free genomic library preparation is used, and the randomly fragmented genomic DNA, e.g., cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about 20-40 bp, e.g., 36 bp, are aligned against a repeat-masked reference genome and unique mapping of the short sequence reads to the reference genome are identified using specially developed data analysis pipeline software. Non-repeat-masked reference genomes can also be used. Whether repeat-masked or non-repeat-masked reference genomes are used, only reads that map uniquely to the reference genome are counted. After completion of the first read, the templates can be regenerated in situ to enable a second read from the opposite end of the fragments. Thus, either single-end or paired end sequencing of the DNA fragments can be used. Partial sequencing of DNA fragments present in the sample is performed, and sequence tags comprising reads of predetermined length, e.g., 36 bp, are mapped to a known reference genome are counted. In one embodiment, the reference genome sequence is the NCBI36/hg18 sequence, which is available on the world wide web at genome.ucsc.edu/cgi-bin/hgGateway?org=Human&db=hg18&hgsid=166260105). Alternatively, the reference genome sequence is the GRCh37/hg19, which is available on the world wide web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software.

In some embodiments of the methods described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence tags comprise sequence reads that are 36 bp. Mapping of the sequence tags is achieved by comparing the sequence of the tag with the sequence of the reference to determine the chromosomal origin of the sequenced nucleic acid (e.g. cfDNA) molecule, and specific genetic sequence information is not needed. A small degree of mismatch (0-2 mismatches per sequence tag) may be allowed to account for minor polymorphisms that may exist between the reference genome and the genomes in the mixed sample.

A plurality of sequence tags are typically obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads, e.g., 36 bp, are obtained from mapping the reads to the reference genome per sample. In one embodiment, all the sequence reads are mapped to all regions of the reference genome. In one embodiment, the tags that have been mapped to all regions, e.g., all chromosomes, of the reference genome are grouped into islands for phasing.

Systems and Apparatus for Determining Genomic Phase Information

Analysis of the sequencing data, including phasing and identifying haplotypes as described herein, are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads derived from a nucleic acid sample, counts or densities of such tags that align with particular regions of a reference sequence (e.g., that align to a chromosome or chromosome segment), separation distances between adjacent reads or fragments, distributions of such separation distances, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for determining one or more haplotypes of a genomic sample. The computer product may contain instructions for performing any one or more of the above-described methods for phasing or haplotyping a segment. As explained, the computer product may include a non-transitory and/or tangible computer readable medium having a computer executable or compilable logic (e.g., instructions) recorded thereon for enabling a processor to align reads, identify fragments and/or islands from aligned reads, identify alleles, including indel alleles, of heterozygous polymorphisms, phase portions of chromosomes, and haplotype chromosomes and genomes. In one example, the computer product comprises (1) a computer readable medium having a computer executable or compilable logic (e.g., instructions) stored thereon for enabling a processor to haplotype or phase a nucleic acid sample; (2) computer assisted logic for sequencing a genomic sample; and (3) an output procedure for generating an output characterizing the sample of an individual providing such sample.

It should be understood that it is not practical, or even possible in most cases, for an unaided human being to perform the computational operations of the methods disclosed herein. For example, aligning a single 30 bp read from a sample to any one of the human chromosomes might require years of effort without the assistance of a computational apparatus. Of course, the problem is compounded because reliable phasing generally require aligning thousands (e.g., at least about 10,000) or even millions of reads to one or more chromosomes.

The methods disclosed herein can be performed using a system for phasing a nucleic acid sample. The system comprising: (a) a sequencer for receiving nucleic acids from the test sample providing nucleic acid sequence information from the sample; (b) a processor; and (c) one or more computer-readable storage media having stored thereon instructions for execution on said processor to evaluate data from the sequencer.

In some embodiments, the methods are instructed by a computer-readable medium having stored thereon computer-readable instructions for carrying out a method for determining the phase of a sequence. Thus one embodiment provides a computer program product comprising one or more computer-readable non-transitory storage media having stored thereon computer-executable instructions that, when executed by one or more processors of a computer system, cause the computer system to implement a method for haplotyping a gDNA sample. The method includes: (i) aligning sequence reads to a reference genome to produce aligned reads, where aligned reads from a first high molecular weight segment tend to cluster into islands on the reference genome; (ii) determining distances separating adjacent ones of the aligned reads on the reference genome, wherein the separation distances between adjacent aligned reads fall into at least two groups distinguishable by the magnitude of their separation distances; (iii) selecting a first group of the aligned reads having separation distances to adjacent aligned reads that are smaller than a cutoff value, thereby excluding aligned reads having greater separation distances, where at least a portion of the first group of the aligned reads belong to the same island on the reference genome; and (iv) using alleles from the first group of aligned reads to define a first haplotype or first partial haplotype. In some embodiments, the computer system is configured to work with other system components such as components for (i) processing the DNA sample to produce an enriched DNA sample enriched for DNA from a first high molecular weight segment having a plurality of alleles from a first haplotype; and (ii) sequencing DNA in the enriched DNA sample to produce a plurality of sequence reads, which are shorter in length than the first high molecular weight segment, wherein some of the sequence reads contain a first allele of the first haplotype and other of the sequence reads contain a second allele of the first haplotype.

In some embodiments, the instructions may further include automatically recording information pertinent to the method such as haplotype blocks and the presence or absence of a genetic disorder in a patient medical record for a human subject providing the sample. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the sample was taken. This may involve performing one or more additional tests or analyses on additional samples taken from the subject.

Disclosed methods can also be performed using a computer processing system which is adapted or configured to perform a method for determining a condition related to a particular haplotype, e.g., a genetic disorder. One embodiment provides a computer processing system which is adapted or configured to perform a method as described herein. In one embodiment, the apparatus comprises a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store reads, tags, fragments, islands, phase information, etc. for various chromosomes or genomes. The memory device may store such information for a plurality of discrete virtual compartments. The memory may also store various routines and/or programs for analyzing and presenting the sequence or aligned data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. For example, reads may be transmitted as they are generated, or soon thereafter, and aligned and other analyzed remotely. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer or dedicated storage device at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:

Reads obtained by sequencing nucleic acids in a nucleic acid sample (these may be indexed or otherwise differentiated from one another on the basis of processing history—e.g., some may grouped based on virtual compartment).

Tags obtained by aligning reads to a reference genome or other reference sequence or sequences The reference genome or sequence Islands or fragments identified for a group of reads having the substantially the same processing history (e.g., the reads from a given virtual compartment).

Diagnoses (clinical condition associated with the calls)

Recommendations for further tests derived from the calls and/or diagnoses

Treatment and/or monitoring plans derived from the calls and/or diagnoses

These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a research laboratory, a forensics laboratory, a doctor's office or other clinical setting, etc. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed for haplotyping. At this remote location, as an example, the reads are aligned to a reference sequence to produce tags, which are segregated into islands and phased. Also at the remote location, the islands may be used to identify partial or full haplotypes. Still further, at the remote location, the haplotypes may be used for clinical or scientific purposes (e.g., association studies).

Among the processing operations that may be employed at distinct locations are the following:

Sample collection

Sample processing preliminary to sequencing

Sequencing

Analyzing sequence data and haplotyping

Diagnosis

Reporting a diagnosis and/or a call to patient or health care provider

Developing a plan for further treatment, testing, and/or monitoring

Executing the plan

Counseling

Any one or more of these operations may be automated as described elsewhere herein. Typically, the sequencing and the analyzing of sequence data and deriving haplotype information will be performed computationally. The other operations may be performed manually or automatically.

Examples of locations where sample collection may be performed include laboratories, research institutions, law enforcement facilities, health practitioners' offices, clinics, patients' homes (where a sample collection tool or kit is provided), and mobile health care vehicles. Examples of locations where sample processing prior to sequencing may be performed include laboratories, research institutions, law enforcement facilities, health practitioners' offices, clinics, patients' homes (where a sample processing apparatus or kit is provided), mobile health care vehicles, and facilities of genetic analysis providers. Examples of locations where sequencing may be performed include laboratories, research institutions, law enforcement facilities, health practitioners' offices, clinics, health practitioners' offices, clinics, patients' homes (where a sample sequencing apparatus and/or kit is provided), mobile health care vehicles, and facilities of genetic analysis providers. The location where the sequencing takes place may be provided with a dedicated network connection for transmitting sequence data (typically reads) in an electronic format. Such connection may be wired or wireless and have and may be configured to send the data to a site where the data can be processed and/or aggregated prior to transmission to a processing site. Data aggregators can be maintained by health organizations such as Health Maintenance Organizations (HMOs).

The analyzing and/or deriving operations may be performed at any of the foregoing locations or alternatively at a further remote site dedicated to computation and/or the service of analyzing nucleic acid sequence data. Such locations include for example, clusters such as general purpose server farms, the facilities of an genetic analysis service business, and the like. In some embodiments, the computational apparatus employed to perform the analysis is leased or rented. The computational resources may be part of an internet accessible collection of processors such as processing resources colloquially known as the cloud. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In certain embodiments, the diagnosis (e.g., the patient has a particular type of cancer) is generated at the same location as the analyzing operation. In other embodiments, it is performed at a different location. In some examples, reporting the diagnosis is performed at the location where the sample was taken, although this need not be the case. Examples of locations where the diagnosis can be generated or reported and/or where developing a plan is performed include health practitioners' offices, clinics, internet sites accessible by computers, and handheld devices such as cell phones, tablets, smart phones, etc. having a wired or wireless connection to a network. Examples of locations where counseling is performed include health practitioners' offices, clinics, internet sites accessible by computers, handheld devices, etc.

In some embodiments, the sample collection, sample processing, and sequencing operations are performed at a first location and the analyzing and deriving operation is performed at a second location. However, in some cases, the sample collection is collected at one location (e.g., a research institution, a health practitioner's office or clinic) and the sample processing and sequencing is performed at a different location that is optionally the same location where the analyzing and deriving take place.

In various embodiments, a sequence of the above-listed operations may be triggered by a user or entity initiating sample collection, sample processing and/or sequencing. After one or more these operations have begun execution the other operations may naturally follow. For example, the sequencing operation may cause reads to be automatically collected and sent to a processing apparatus which then conducts, often automatically and possibly without further user intervention, the sequence analysis and derivation of phase or haplotype information. In some implementations, the result of this processing operation is then automatically delivered, possibly with reformatting as a report or diagnosis, to a system component or entity that processes reports the information to a researcher, health professional and/or patient. As explained such information can also be automatically processed to produce a treatment, testing, and/or monitoring plan, possibly along with counseling information. Thus, initiating an early stage operation can trigger an end to end sequence in which the health professional, patient or other concerned party is provided with a diagnosis, a plan, counseling and/or other information useful for acting on a physical condition. This is accomplished even though parts of the overall system are physically separated and possibly remote from the location of, e.g., the sample and sequence apparatus.

Figure 8:
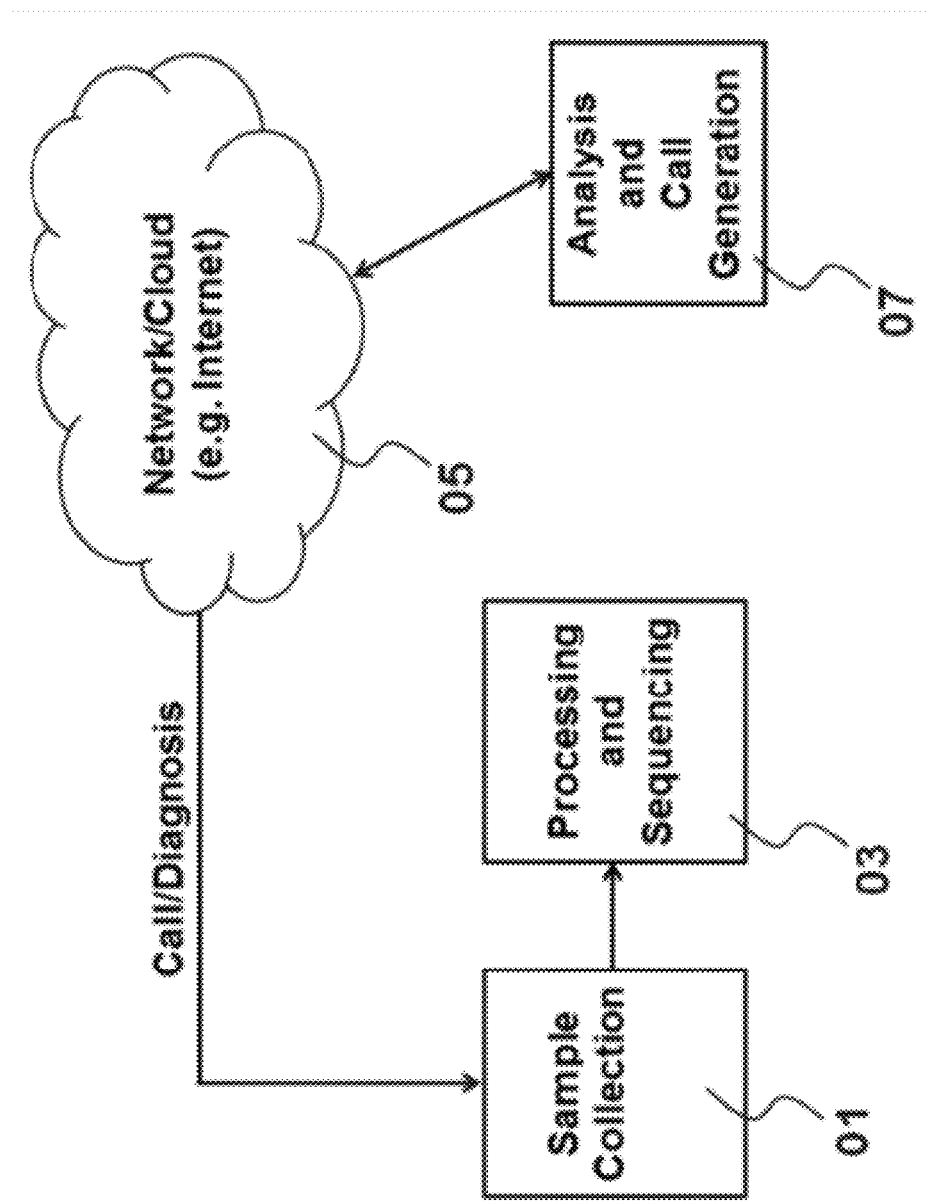
FIG. 8—This figure is a block diagram of a dispersed system for processing a sample and ultimately making a diagnosis or other conclusion based on a haplotype determined from the sample.

FIG. 8 shows one implementation of a dispersed system for producing a call or diagnosis from a test sample. A sample collection location 01 is used for obtaining or receiving a sample from a patient such as a pregnant female or a putative cancer patient. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 8.

The sequence data (and possibly the reads themselves) is provided to a remote location 07 where analysis and call generation are performed. This location may include one or more computational devices such as computers or processors. After the computational resources at location 07 have completed their analysis and generated haplotype information from the received sequence information, the haplotype information is relayed back to the network 05. In some implementations, not only is haplotype information generated at location 07 but an associated diagnosis or research conclusion is also generated. The haplotype information and/or conclusion are then transmitted across the network and back to the sample collection location 01 as illustrated in FIG. 8. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and haplotype generation.

Figure 9:
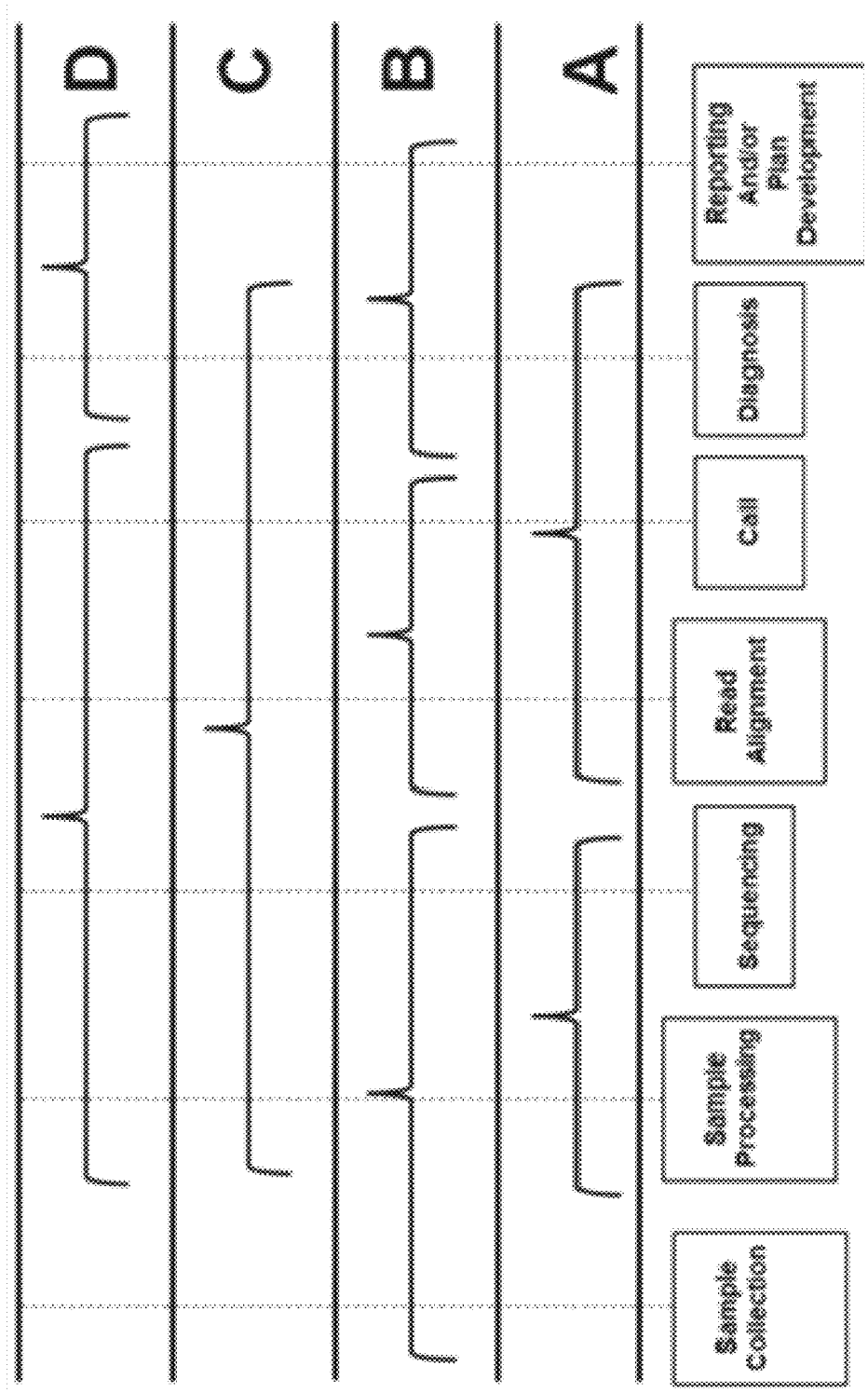
FIG. 9—This figure schematically illustrates how different operations in processing samples may be grouped to be handled by different elements of a system.

FIG. 9 elaborates on the options for performing various operations at distinct locations. In the most granular sense depicted in FIG. 9, each of the following operations is performed at a separate location: sample collection, sample processing, sequencing, read alignment, calling, diagnosis, and reporting and/or plan development.

In one embodiment that aggregates some of these operations, sample processing and sequencing are performed in one location and read alignment, calling, and diagnosis are performed at a separate location. See the portion of FIG. 9 identified by reference character A. In another implementation, which is identified by character B in FIG. 9, sample collection, sample processing, and sequencing are all performed at the same location. In this implementation, read alignment and calling are performed in a second location.

Finally, diagnosis and reporting and/or plan development are performed in a third location. In the implementation depicted by character C in FIG. 9, sample collection is performed at a first location, sample processing, sequencing, read alignment, calling—and diagnosis are all performed together at a second location, and reporting and/or plan development are performed at a third location. Finally, in the implementation labeled D in FIG. 9, sample collection is performed at a first location, sample processing, sequencing, read alignment, and calling are all performed at a second location, and diagnosis and reporting and/or plan management are performed at a third location.

One embodiment provides a system for use in determining a haplotype from a genomic DNA sample, the system including a sequencer for receiving a nucleic acid sample and providing nucleic acid sequence information from the sample; a processor; and a machine readable storage medium comprising instructions for execution on said processor, the instructions comprising: (a) sequencing a DNA sample including first and second indel alleles at the site of a heterozygous indel polymorphism, wherein the sequencing produces a plurality of sequence reads, including at least a first read containing the sequence of the first indel allele and a second read containing the sequence of the second indel allele; (b) examining the sequence reads, including the first read and the second read, to identify and characterize polymorphisms including the first indel polymorphism, wherein each of the plurality of heterozygous polymorphisms is characterized by a genome location and sequences of each allele; (c) modifying a reference genome to produce two pseudo-reference genomes, a first pseudo-reference genome containing the first indel allele at the genome location of the heterozygous indel polymorphism, and a second pseudo-reference genome containing the second indel allele at the genome location of the heterozygous indel polymorphism; (d) aligning the first read to the first and second pseudo-reference genomes and determining which of the two pseudo-reference genomes provides the better alignment, and selecting the indel allele of the pseudo-reference genome as belonging to the first segment, wherein the first read is from the first segment; and (e) developing a partial or complete haplotype from the alleles of the first segment, wherein one allele of the haplotype is the indel allele selected in (d).

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method of determining a haplotype or partial haplotype of a DNA sample comprising high molecular weight segments of genomic DNA, the method comprising:
processing the DNA sample to produce an enriched DNA sample enriched for DNA from a first high molecular weight segment having a plurality of alleles from a first haplotype;
sequencing DNA in the enriched DNA sample to produce a plurality of sequence reads, which are shorter in length than the first high molecular weight segment, wherein some of the sequence reads contain a first allele of the first haplotype and other of the sequence reads contain a second allele of the first haplotype;
aligning the sequence reads to a reference genome to produce aligned reads, wherein aligned reads from the first high molecular weight segment tend to cluster into islands on the reference genome;
determining distances separating adjacent ones of the aligned reads on the reference genome, wherein the separation distances between adjacent aligned reads fall into at least two groups distinguishable by the magnitude of their separation distances;
determining a cutoff value by (i) generating a mixture model from the separation distances between adjacent aligned reads, wherein the mixture model fits two Gaussian distributions to the separation distances; and (ii) determining the cutoff value from a property of at least one of the two Gaussian distributions;
selecting a first group of the aligned reads having separation distances to adjacent aligned reads that are smaller than the cutoff value, thereby excluding aligned reads having greater separation distances, wherein at least a portion of the first group of the aligned reads belong to the same island on the reference genome; and
using alleles from the first group of aligned reads to define a first haplotype or first partial haplotype.

2. The method of claim 1, further comprising determining a complete haplotype from the first partial haplotype and other partial haplotypes.

3. The method of claim 1, wherein the high molecular weight segments are at least about 50 kb in length on average.

4. The method of claim 1, wherein the high molecular weight segments are at least about 100 kb in length on average.

5. The method of claim 1, wherein each of the two Gaussian distributions comprises its own central tendency.

6. The method of claim 1, wherein generating a mixture model comprises applying an expectation maximization procedure to the separation distances between adjacent aligned reads.

7. The method of claim 1, wherein determining the cutoff value comprises identifying a fraction of the probability mass of the distribution containing the shorter separation distances.

8. The method of claim 7, wherein the fraction of the probability mass of the distribution containing the shorter separation distances is about 80% or greater.

9. A system for haplotyping genomic DNA samples comprising:

(a) a sequencer for receiving nucleic acids samples and providing nucleic acid sequence information from the sample;
(b) a processor; and
(c) one or more computer-readable storage media having stored thereon instructions for execution on said processor to evaluate sequence reads from the sequencer, the instructions comprising:
  (i) aligning the sequence reads to a reference genome to produce aligned reads, wherein aligned reads from a first high molecular weight segment of a genomic DNA sample tend to cluster into islands on the reference genome;
  (ii) determining distances separating adjacent ones of the aligned reads on the reference genome, wherein the separation distances between adjacent aligned reads fall into at least two groups distinguishable by the magnitude of their separation distances;
  (iii) determining a cutoff value by
    generating a mixture model from the separation distances between adjacent aligned reads, wherein the mixture model fits two Gaussian distributions to the separation distances; and
    determining the cutoff value from a property of at least one of the two Gaussian distributions;
  (iv) selecting a first group of the aligned reads having separation distances to adjacent aligned reads that are smaller than the cutoff value, thereby excluding aligned reads having greater separation distances, wherein at least a portion of the first group of the aligned reads belong to the same island on the reference genome; and
  (v) using alleles from the first group of aligned reads to define a first haplotype or first partial haplotype.

10. The system of claim 9, further comprising a component configured to process a DNA sample to produce an enriched DNA sample enriched for DNA from the first high molecular weight segment having a plurality of alleles from a first haplotype.

* * * * *